US009574212B2

(12) United States Patent
Foody et al.

(10) Patent No.: US 9,574,212 B2
(45) Date of Patent: Feb. 21, 2017

(54) PROCESS COMPRISING SULFUR DIOXIDE AND/OR SULFUROUS ACID PRETREATMENT AND ENZYMATIC HYDROLYSIS

(71) Applicant: Iogen Corporation, Ottawa (CA)

(72) Inventors: Brian Foody, Ottawa (CA); Jeffrey S. Tolan, Ottawa (CA); Daniel MacDonald, Ottawa (CA); Patrick J. Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

(21) Appl. No.: 15/199,638

(22) Filed: Jun. 30, 2016

(65) Prior Publication Data

US 2016/0312249 A1    Oct. 27, 2016

Related U.S. Application Data

(63) Continuation-in-part of application No. PCT/CA2016/050291, filed on Mar. 16, 2016.

(60) Provisional application No. 62/269,339, filed on Dec. 18, 2015, provisional application No. 62/142,068, filed on Apr. 2, 2015, provisional application No. 62/133,609, filed on Mar. 16, 2015.

(51) Int. Cl.
*C12P 7/14*      (2006.01)
*C12P 7/10*      (2006.01)
*C12P 19/02*     (2006.01)
*C12P 19/14*     (2006.01)
*C12M 1/00*      (2006.01)
*D21C 1/02*      (2006.01)
*D21C 1/04*      (2006.01)
*B01D 53/00*     (2006.01)

(52) U.S. Cl.
CPC ............... *C12P 7/14* (2013.01); *C12M 45/03* (2013.01); *C12M 45/09* (2013.01); *C12M 45/20* (2013.01); *C12P 7/10* (2013.01); *C12P 19/02* (2013.01); *C12P 19/14* (2013.01); *C12Y 302/01004* (2013.01); *D21C 1/02* (2013.01); *D21C 1/04* (2013.01); *B01D 53/002* (2013.01); *B01D 2257/302* (2013.01); *C12P 2201/00* (2013.01)

(58) Field of Classification Search
CPC .......... C07C 45/59; C07C 45/60; C07C 37/54; C07C 41/01; C07C 49/395; C07C 49/597; C07C 49/84; C07C 49/403; C07C 49/825; C07C 29/00; C07C 67/00; C07C 43/23; C07C 35/08; C07C 39/04; C07C 39/06; C07C 69/06; C07C 39/07; C07C 1/045; C07C 37/004; C07C 37/72; C07C 37/74; C07C 9/04; C07C 1/04; C07C 37/68; C10G 2/32; C10G 45/00; C10J 2300/0916; C10J 2300/1681; C10J 3/00; C10J 2300/0906; C10J 2300/0959
See application file for complete search history.

(56) References Cited

U.S. PATENT DOCUMENTS

| | | | |
|---|---|---|---|
| 2,418,167 A | 4/1947 | Du Bois | |
| 5,789,210 A | 8/1998 | Ho et al. | |
| 5,866,382 A | 2/1999 | Hallborn et al. | |
| 6,475,768 B1 | 11/2002 | Otero et al. | |
| 6,582,944 B1 | 6/2003 | Hallborn et al. | |
| 7,527,927 B1 | 5/2009 | Ho et al. | |
| 7,527,951 B2 | 5/2009 | Londesborough et al. | |
| 7,622,284 B2 | 11/2009 | Op Den Camp et al. | |
| 8,038,842 B2 | 10/2011 | Retsina et al. | |
| 8,268,125 B2 | 9/2012 | Retsina et al. | |
| 8,409,836 B2 | 4/2013 | Vehmaanpera et al. | |
| 8,709,770 B2 | 4/2014 | Harlick et al. | |
| 8,728,243 B2 | 5/2014 | Van Der Meulen et al. | |
| 8,815,499 B2 | 8/2014 | Alriksson et al. | |
| 8,834,633 B2 | 9/2014 | van der Meulen et al. | |
| 8,871,475 B2 | 10/2014 | Alriksson et al. | |
| 9,012,188 B2 | 4/2015 | Van Heiningen et al. | |

(Continued)

FOREIGN PATENT DOCUMENTS

| | | |
|---|---|---|
| WO | 2006/034590 A1 | 4/2006 |
| WO | 2006/034591 A1 | 4/2006 |

(Continued)

OTHER PUBLICATIONS

International Search Report and Written Opinion in PCT Application No. PCT/CA2016/050291, mailed on Jun. 7, 2016.
Shevchenko et al., "Optimization of monosaccharide recovery by post-hydrolysis of the water-soluble hemicellulose component after steam explosion of softwood chips," 2000, Bioresource Technology, pp. 207-211, vol. 72.
Shevchenko et al., "The Nature of Lignin from Steam Explosion/Enzymatic Hydrolysis of Softwood," 1999, Applied Biochemistry and Biotechnology, pp. 867-876, vol. 77-79.

(Continued)

*Primary Examiner* — Debbie K Ware
(74) *Attorney, Agent, or Firm* — Knobbe Martens Olson & Bear LLP

(57) ABSTRACT

The disclosure provides a process for producing a fermentation product from a lignocellulosic feedstock. The process describes soaking a lignocellulosic feedstock in an aqueous solution to produce a soaked feedstock. The soaked feedstock is at least partially dewatered and the at least partially dewatered feedstock is subjected to pretreating in the presence of sulfur dioxide, sulfurous acid or a combination thereof to produce a pretreated feedstock composition. The pretreated feedstock composition is fed to an enzymatic hydrolysis in which the concentration of dissolved solids fed to the enzymatic hydrolysis is at least 50% (w/w) of the concentration of dissolved solids in the pretreated feedstock composition. The cellulose in the pretreated feedstock composition is hydrolyzed with cellulase enzymes in the presence of the dissolved solids to produce glucose. The glucose is fermented to produce the fermentation product.

20 Claims, 2 Drawing Sheets

(56) References Cited

U.S. PATENT DOCUMENTS

| | | | |
|---|---|---|---|
| 9,090,915 | B2 | 7/2015 | Wang et al. |
| 9,102,951 | B2 | 8/2015 | Griffin et al. |
| 9,290,821 | B2 | 3/2016 | Blackbourn et al. |
| 2009/0118477 | A1 | 5/2009 | Hallberg et al. |
| 2010/0056774 | A1 | 3/2010 | Anand et al. |
| 2010/0279361 | A1 | 11/2010 | South et al. |
| 2011/0300586 | A1 | 12/2011 | Liu et al. |
| 2012/0041186 | A1 | 2/2012 | Pschorn et al. |
| 2013/0071903 | A1 | 3/2013 | Rowland et al. |
| 2014/0053827 | A1 | 2/2014 | Baudel et al. |
| 2014/0154746 | A1 | 6/2014 | Jonsson et al. |
| 2014/0163210 | A1 | 6/2014 | Retsina et al. |
| 2014/0178944 | A1* | 6/2014 | Parekh ............... C12P 19/02 435/99 |
| 2014/0182582 | A1 | 7/2014 | Retsina et al. |
| 2014/0186899 | A1 | 7/2014 | Retsina et al. |
| 2015/0259709 | A1 | 9/2015 | Retsina et al. |

FOREIGN PATENT DOCUMENTS

| | | |
|---|---|---|
| WO | 2006/128304 A1 | 12/2006 |
| WO | 2008/041840 A1 | 4/2008 |
| WO | 2010/022511 A1 | 3/2010 |
| WO | 2013/113579 A1 | 8/2013 |
| WO | 2014/106222 A2 | 7/2014 |

OTHER PUBLICATIONS

Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.

Shuai et al., "Comparitive study of SPORL and dilute-acid pretreatments of spruce for cellulosic ethanol production," 2010, Bioresource Technology, pp. 3106-3114, vol. 2010.

Sipos et al., "Steam pretreatment of dry and ensiled industrial hemp for ethanol production," 2010, Biomass and Bioenergy, pp. 1-11.

Soderstrom et al. "Effect of Washing on Yield in One- and Two-Step Steam Pretreatment of Softwood for Production of Ethanol," 2004, Biotehncol. Prog., pp. 744-749, vol. 20.

Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.

Soderstrom et al. "Two-Step Steam Pretreatment of Softwood with SO2 Impregnation for Ethanol Production," 2002, Applied Biochemistry and Biotechnology, pp. 5-21, vol. 98-100.

Szengyel et al., "Cellulase Production of Trichoderma reesei Rut C 30 Using Steam-Penetrated Spruce," 2000, Applied Biochemistry and Biotechnology, pp. 679-691, vol. 84-86.

Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.

Tengborg et al., "Reduced inhibition of enzymatic hydrolysis of steam-pretreated softwood," 2001, Enzyme and Microbial Technology, pp. 835-844, vol. 28.

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain Saccharomuces cerevisiae without detoxification," 2010, Bioresource Technology, pp. 8678-8685, vol. 101.

Trajano et al. "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergetic effects of mixing hybrid poplar and wheat straw biomass for bioconversion processes," 2015, Biotechnol Biofuels, pp. 1-10, vol. 8:226.

Von Sivers et al., "A Techno-Economical Comparison of Three Processes for the Production of Ethanol from Pine," 1995, Bioresource Technology, pp. 43-52, vol. 51.

Wang et al., "Lignosulfonate and elevated pH can enhance enzymatic saccharification of lignocelluloses," 2013, Biotechnology for Biofuels, pp. 1-10, vol. 6:9.

Wang et al., "Ethanol production from poplar wood through enzymatic saccharification and fermentation by dilute acid and SPORL pretreatments," 202, Fuel, pp. 606-614, vol. 95.

Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.

Wayman et al., "Hydrolysis of Biomass by Sulphur Dioxide," 1984, Biomass, pp. 183-191, vol. 6.

Wayman et al., "SO2 Catalysed Prehydrolysis of Coniferous Wood for Ethanol Production," 1986, Biotechnology Letters, pp. 749-752, vol. 8, No. 10.

Wiman et al., "Cellulose accessibility determines the rate of enzymatic hydrolysis of steam-pretreated spruce," 2012, Bioresource Technology, pp. 208-215, vol. 126.

Wolfinger et al., "Modeling of the Acid Sulfite Pulping Process.—Problem Definition and Theoretical Approach for a solution with the Main Focus on the Recovery of Cooking Chemicals," 2004, Lenzinger Berichte, pp. 35-45, vol. 83.

Wooley, Bob, "Production of 1,000 Gallons of BioJet," 2015, Presentation from 2015 Annual Meeting of Northwest Advanced Renewables Alliance (NARA).

Wyman et al., "Comparative data on effects of leading pretreatments and enzyme loadings and formulations on sugar yields from different switchgrass sources," 2011, Bioresource Technology, 11052-11062, vol. 102.

Wyman et al., "Comparative Sugar Recovery and Fermentation Data Following Pretreatment of Poplar Wood by Leading Technologies," 2009, Biotechnol. Prog., pp. 333-339, vol. 25, No. 2.

Fan et al., "Optimization of SO2-catalyzed hydrolysis of corncob for xylose and xylitol production," 2014, J Chem Technol Biotechnol, pp. 1720-1726, vol. 89.

Zhang et al., "Sulfite (SPORL) pretreatment of switchgrass for enzymatic saccharification," 2013, Bioresource Technology, pp. 127-134, vol. 129.

Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.

Zhu et al , "Woody biomass pretreatment for cellulosic ethanol production: Technology and energy consumption evaluation," 2010, Bioresource Technology, pp. 4992-5002, vol. 101.

Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.

Zhu et al., "Ethanol production from SPORL-pretreated lodgepole pine: preliminary evaluation of mass balance and process energy efficiency," 2010, Appl Microbiol Biotechnol, pp. 1355-1365, vol. 86.

Zhu et al., "High Titer Ethanol Production from Forest Residue Using Sulfite Mill Pulping Chemistry," 2015, Presentation at 2015 TAPPI IBBC.

Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.

Zhu et al., "On Polydispersity of Plant Biomass Recalcitrance and Its Effects on Pretreatment Optimization for Sugar Production," 2011, Bioenerg. Res., pp. 201-210, vol. 4.

Zhu et al., Quantitative predictions of bioconversion of aspen by dilute acid and SPORL pretreatments using a unified Combined hydrolysis factor (CHF), 2012, Process Biochemistry, pp. 785-791, vol. 47.

Zhu et al., "Sulfite pretreatment (SPORL) for robust enzymatic saccharification of spruce and red pine," 2009, Bioresource Technology, pp. 2411-2418, vol. 100.

(56) References Cited

OTHER PUBLICATIONS

Bensah, E. and Mensah, M., "Chemical Pretreatment Methods for the Production of Cellulosic Ethanol: Technologies and Innovations," International Journal of Chemical Engineering, 2013, pp. 1-21, vol. 2013.
Bhalla, A. et al., "Improved lignocellulose conversion to biofuels with thermophilic bacteria and thermostable enzymes," Bioresource Techonologoy, 2013, pp. 751-759, vol. 128.
Boussaid, A., et al., "Fermentability of the Hemicellulose-Derived Sugars from Steam-Exploded Softwood (Douglas Fir)," , Biotechnology and Biogengineering, 1999, pp. 284-289, vol. 64, No. 3.
Brownell, H. and Saddler, J., "Steam Pretreatment of Lignocellulosic Material for Enhanced Enzymatic Hydrolosis," Biotechnology and Bioengineering, 1987, pp. 228-235, vol. 29.
Bura, et al., "Moving towards commercialization of lignocellulosic biomass to fuels to chemicals. How to deal with heterogeneous biomass?" University of Washington Biofuels and Bioproducts Laboratory, 2012.
Bura, R., et al., "Influence of Xylan on the Enzymatic Hydolysis of Steam-Pretreated Corn Stover and Hybrid Poplar," Biotechnol Prog, 2009, pp. 315-322, vol. 25, No. 2.
Bura, R., et al., "$SO_2$-Catalyzed Steam Explosion of Corn Fiber for Ethanol Production", Applied Biochemistry and Biotechnology, 2002, pp. 59-72, vols. 98-100.
Carrasco, C., et al., "$SO_2$-catalysed steam pretreatment of quinoa stalks," J Chem Technol Biotechnol, 2015, pp. 54-71, vol. 90.
Carrasco, C., et al., "$SO_2$-catalyzed steam pretreatment and fermentation of enzymatically hydrolyzed sugarcane bagasse," Enzyme and Microbial Technology, 2010, pp. 64-73, vol. 46.
Carrasco, C., "Arabinosylated phenolics obtained from $SO_2$-steam-pretreated sugarcane bagasse," Journal of Chemical Technology and Biotechnology, 2012, pp. 1723-1726, vol. 87.
Chacha, N., et al., "Steam Pretreatment of Pine (*Pinus patula*) Wood Residue for the Production of Reducing Sugars," Cellulose Chemistry and Technology, 2011, pp. 495-501, vol. 45 (7-8).
Chandra, R., et al., "Enhancing Hemicellulose Recovery and the Enzymatic Hydrolysis of Celllulose by Adding Lignosulfonates during the Two-Stage Steam Pretreatment of Poplar," ACS Sustainable Chem Eng, 2015, pp. 386-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Clark, T.A. et al., "Steam Explosion of the Softwood Pinus Radiata with Sulphur Dioxide Addition. II. Process Charactisation," Journal of Wood Chemistry and Technology, 1989, pp. 135-166, vol. 9:2.
Clark, T.A. et al., "Steam Explosion of the Softwood Pinus Radiata with Sulphur Dioxide Addition. I. Process Optimization," Journal of Wood Chemistry and Technology, 1987, pp. 373-403, vol. 7:3.
Corrales et al., "Structural evaluation of sugar cane bagasse steam pretreated in the presence of $CO_2$ and $SO_2$," Biotechnology for Biofuels, 2012, pp. 1-8, vol. 5:36.
De Bari et al., "$SO_2$-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H. et al., "Enzymic Saccharification of Sugarcase Bagasse Pretreated by Autohydrolosys-Steam Explosion," Biotechnology and Bioengineering, 1983, pp. 3027-3048, vol. XXV.
Dekker, Robert F. H., "The Utilization of Autohydrolysis-Exploded Hardwood (Eucalyptus Regnans) and Softwood (Pinus Radiata) Sawdust for the Production of Cellulolytic Enzymes and Fermentable Substrates," Biocatalysis, 1987, pp. 63-75, vol. 1.
Ehsanipour, Mandana "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of $SO_2$ and $H_2SO_4$ Impregnation of Willow Prior to Steam Pretreatment," 1995, Bioresource Engineering, pp. 225-229, vol. 52.

Elander, et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Galbe et al., "A review of the production of ethanol from softwood," 2002, Appl Microbial Biotechnol, pp. 618-628, vol. 59.
Garlock et al., "Comparative material balances around pretreatment technologies for the conversion of switchgrass to soluble sugars," 2011, Bioresource Technology, pp. 11063-11071, vol. 102.
Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.
Gu et al., "Fermentative High-Titer Ethanol Production from Douglas-Fir Forest Residue Without Detoxification Using SPORL: High $SO_2$ Loading at Low Temperature," 2016, Industrial Biotechnology, pp. 168-175, vol. 12, No. 3.
Hodge et al., "Soluble and insoluble solids contributions to high-solids enzymatic hydrolysis of lignocellulose," 2008, Bioresource Technology, pp. 8940-8948, vol. 99.
Kumar et al., "Access of Cellulase to Cellulose and Lignin for Poplar Solids Produced by Leading Pretreatment Technologies," 2009, Biotechnol. Prog., pp. 807-819, vol. 25, No. 3.
Lan et al., "High titer ethanol production from SPORL-pretreated lodgepole pine by simultaneous enzymatic saccharification and combined fermentation," 2013, Bioresource Technology, pp. 291-297, vol. 127.
Leu et al., "Substrate-Related Factors Affecting Enzymatic Saccharification of Lignocelluloses; Our Recent Understanding," 2013, Bioenerg. Res., pp. 405-415, vol. 6.
Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).
Mackie et al., "Effect of Sulphur Dioxide and Sulphuric Acid on Steam Explosion of Aspenwood," 1985, Journal of Wood Chemistry and Technology, pp. 405-425, vol. 5(3).
Mamers et al., "Explosion preteatment of Pinus radiata woodchips for the production of fermnation substrates," 1984, Apita, pp. 644-649, vol. 37.
Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.
Monavari et al., "Improved One-Step Steam Pretreatment if $SO_2$-Impregnated Softwood with Time-Dependant Temperature Profile for Ethanol Production," 2010, Biotechnol. Prog., pp. 1054-1060, vol. 26, No. 4.
Nguyen et al., "Dilute Acid Pretreatment of Softwoods," 1998, Applied Biochemistry and Biotechnology, pp. 77-89, vol. 70-72.
Nguyen et al., "Two-Stage Dilute Acid Pretreatment of Softwoods," 2000, Applied Biochemistry and Biotechnology, 561-576, vol. 84-86.
Ohgren et al., "Optimization of Steam Pretreatment of $SO_2$-Impregnated Corn Stover for Fuel Ethanol Production," 2005, Applied Biochemistry and Biotechnology, pp. 1055-1067, vol. 121-124.
Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.
Rakkolainen et al., "$SO_2$-Ethanol-Water Fractionation of Forest Biomass and Implications for Biofuel Production by Abe Fermentaion," 2010, Cellulose Chem. Technol., pp. 19-145, vol. 44.
Ramos et al. "Characterization of Residual Lignin after $SO_2$-Catalyzed Steam Explosion and Enzymatic Hydrolosis of Eucalyptus viminalis Wood Chips," 1999, J. Agric. Food Chem., pp. 2295-2302, vol. 47.
Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.

(56) References Cited

OTHER PUBLICATIONS

Ramos et al., "Effect of enzymatic hydrolysis on the morphology and fine structure of pretreated cellulosic residues," 1993, Enzyme Microb. Technol., pp. 821-831, vol. 15.
Sassner et al., "Steam Pretreatment of Salix with and without SO2 Impregnation for Production of Bioethanol," 2005, Applied Biochemistry and Biotechnology, pp. 1101-1117, vol. 121-124.
Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.
Schell et al., "Pretreatment of Softwood by Acid-Catalyzed Steam Explosion Followed by Alkali Extraction," 1998, Applied Biochemistry and Biotechnology, pp. 17-24, vol. 70-72.
Schwald et al., "Assessment of Pretreatment Conditions to Obtain Fast Complete Hydrolysis on High Substrate concentrations," 1989, Applied Biochemistry and Biotechnology, pp. 29-44, vol. 21/21.
Sendelius et al., "Steam Pretreatment Optimisation for Sugarcane Bagasse in Bioethanol Production," 2005, Master of Science Thesis, Lund University, Sweden.

\* cited by examiner

PROCESS COMPRISING SULFUR DIOXIDE AND/OR SULFUROUS ACID PRETREATMENT AND ENZYMATIC HYDROLYSIS

CROSS-REFERENCE TO RELATED APPLICATIONS

This application is a continuation-in-part of International Appl. No. PCT/CA2016/050291 filed Mar. 16, 2016, which claims the priority benefit of provisional application No. 62/133,609, filed Mar. 16, 2015, provisional application No. 62/142,068, filed Apr. 2, 2015, and provisional application No. 62/269,339, filed Dec. 18, 2015, all of which are incorporated herein by reference.

TECHNICAL FIELD

The present invention provides a process for producing one or more products from a lignocellulosic feedstock by a process comprising sulfur dioxide and/or sulfurous acid pretreatment and enzymatic hydrolysis.

BACKGROUND

The production of fuel ethanol, or other fuels and chemicals, from lignocellulosic feedstocks provides an attractive alternative to the feedstocks predominantly used to date such as corn starch, sugar cane, and sugar beets. The production of fermentation products from these latter sources cannot increase much further as most of the farmland suitable for the production of these crops is in use. Cellulose is an abundant natural polymer, so there is an enormous untapped potential for its use as a source for fuels and chemicals. Also, lignocellulosic feedstocks to be used for fuel or chemical production are inexpensive as they have limited use. Another advantage of using these feedstocks for fuel or chemical production is that lignin, which is a byproduct of the cellulose conversion process, can be used as a fuel to power the conversion process, thereby avoiding the use of fossil fuels. Several studies have concluded that, when the entire production and consumption cycle is taken into account, the use of ethanol produced from cellulose generates close to nil greenhouse gases.

The conversion of lignocellulosic feedstocks to a fermentation product is usually carried out with a pretreatment process prior to subsequent biological treatments. Pretreatment is usually carried out with addition of a chemical such as an acid or alkali to make the feedstock more amenable to subsequent enzymatic hydrolysis with cellulase enzymes to liberate glucose. The pH of the pretreated feedstock composition resulting from the pretreatment is adjusted to a pH that is suitable for the cellulase enzymes used to produce glucose. The cellulase enzymes then convert the cellulose to glucose and the glucose can then be converted to a fermentation product including ethanol or other fuels or chemicals by yeast or bacterium using known methods. However, one problem with known methods for producing glucose from lignocellulosic feedstocks is that the enzyme requirement is high, which adds significant cost and impedes its commercialization.

Pretreatment of lignocellulosic feedstocks with dilute sulfuric acid at elevated temperature is described in the literature. Pretreatment with sulfuric acid produces an aqueous pretreated feedstock composition in which a large amount of soluble degradation products are present including phenolic lignin and furfural. These compounds inhibit and/or inactivate the cellulase enzymes and thus are most advantageously diluted by adding water, or removed by washing the aqueous pretreated feedstock composition with water prior to carrying out enzymatic hydrolysis. Alternatively, the compounds are removed by treating the liquor by precipitation with lime or other alkali at pH above 8, or by microfiltration methods such as nanofiltration. Unfortunately, there is significant capital and operating cost associated with these processes.

Another chemical pretreatment that has received attention in recent years is pretreatment with sulfur dioxide. Sulfur dioxide is a gas, but when it is dissolved in water, it forms sulfurous acid. Sulfur dioxide and/or sulfurous acid can be added to the lignocellulosic feedstock prior to or during a pretreatment by any of a number of methods, including adding sulfur dioxide gas to the lignocellulosic feedstock or combining dilute sulfurous acid to the lignocellulosic feedstock. Sulfur dioxide and/or sulfurous acid has been reported for use in pretreating dry, presteamed, or prewetted feedstocks such as wood chips. As with sulfuric acid, sulfur dioxide and/or sulfurous acid pretreatment produces soluble compounds that are inhibitory and/or inactivating to cellulase enzymes. These compounds are often diluted with water to decrease the concentration thereof, or removed by washing with water, prior to hydrolysis. The compounds can alternatively be removed by treating the liquor with precipitation using alkali such as lime or by a microfiltration technique, as described previously in connection with sulfuric acid pretreatment. Similar to sulfuric acid pretreatment, there is significant capital and operating cost associated with these processes.

SUMMARY OF THE INVENTION

Some embodiments of the invention seek to overcome these disadvantages, or provide one or more alternatives to known processes for producing products from a lignocellulosic feedstock.

Some embodiments of the invention are based on the discovery that when pretreatment of a lignocellulosic feedstock with sulfur dioxide and/or sulfurous acid is carried out on a soaked, partially dewatered feedstock, it eliminates or reduces the need for water dilution and/or washing of the pretreated feedstock composition prior to hydrolysis, or the use of other expedients such as alkali precipitation or microfiltration of the liquor. When this pretreatment is carried out on a lignocellulosic feedstock, it has been found that maintaining the full concentration of dissolved solids does not significantly reduce the performance of enzymatic hydrolysis to produce glucose. In particular, the inventors have found that the enzymatic hydrolysis of cellulose to glucose with cellulose enzymes without washing of such pretreated feedstock, or alkali precipitation or microfiltration of the liquor, could perform almost as well as a hydrolysis conducted on a pretreated feedstock composition produced by the same pretreatment, but that is washed.

Reducing or eliminating washing and/or water dilution of the pretreated feedstock composition is advantageous. It has been recognized by the inventors that washing steps are particularly difficult to carry out because the pretreated feedstock solids in the composition may contain fine particles that require the use of specialized and costly equipment. Further, increased water usage due to washing and/or water dilution can significantly increase the cost of the process, which is especially problematic in arid regions where water is not readily available. Thus, reducing or eliminating washing and/or dilution of the pretreated feedstock composition is advantageous in that it can avoid costly equipment as well as the cost associated with water usage. For example, eliminating or reducing washing may reduce water usage, whereas eliminating or reducing dilution of the pretreated sample, may allow smaller and/or fewer hydrolysis tanks to be used. In addition, eliminating or reducing washing may allow the C5/C6 sugars produced in pretreatment to be carried through to the fermentation (e.g., without being separated from the pretreatment solids), thus simplifying the process. Further, the costs of processing the liquor with alkali precipitation or microfiltration are also avoided.

Some embodiments of the invention may also result in the usage of less cellulose enzyme, which could further reduce cost, and/or provide improvements in xylose yield from the pretreatment.

In further embodiments of the invention, the feedstock is subjected to soaking in an aqueous solution prior to the pretreating step. The aqueous solution may be water, in which case sulfur dioxide and/or sulfurous acid is added downstream of soaking. Alternatively, the aqueous solution may comprise sulfurous acid due to the addition of sulfurous acid and/or sulfur dioxide during soaking or upstream of the soaking step. Further, sulfur dioxide and/or sulfurous acid can be added both during soaking and also downstream of soaking. That is, regardless of the addition point, the pretreating is conducted in the presence of sulfur dioxide and/or sulfurous acid. Notably, although sulfur dioxide and/or sulfurous acid are discussed herein as "added" at various points of the process and/or to the lignocellulosic feedstock, this term is not intended to indicate an order of addition. For example, as used herein the phrase "sulfur dioxide is added" and/or "sulfurous acid is added" encompasses embodiments wherein the acid is added to lignocellulosic feedstock and/or embodiments wherein the lignocellulosic feedstock is added to the acid.

A benefit of soaking the feedstock prior to pretreatment, whether with an aqueous solution comprising sulfurous acid or with water, followed by later addition of sulfurous acid and/or sulfur dioxide, is that it prepares the feedstock for a subsequent step of pretreatment. For example, in certain embodiments of the invention, soaking may ensure uniform impregnation of the feedstock with the pretreatment chemical. This in turn may ensure that some material is not overcooked and degraded due to the high localized concentration of the pretreatment chemical, while other material is not undercooked, resulting in low xylose yield and difficult cellulose hydrolysis. Undercooking or overcooking of lignocellulosic feedstock can be particularly problematic when the pretreatment is conducted under medium or high solids consistency because the non-uniformity of the concentration of the pretreatment chemical and the temperature are more pronounced. In certain embodiments, the aqueous solution used for soaking can be removed by a step that at least partially dewaters the feedstock. The aqueous solution can then be introduced back to the soaking step, thereby saving on chemical and water usage. Thus, the addition of water as part of a soaking step can result in improved economics compared to a similar process that instead introduces water in a washing step after pretreatment. As described above, washing after pretreatment can require costly equipment and increased water usage. By contrast, the dewatering and liquid recycle in soaking can facilitate improved handling of the liquid.

Thus, according to one aspect of the invention there is provided a process for producing a fermentation product from a lignocellulosic feedstock comprising: (i) soaking the lignocellulosic feedstock in an aqueous solution to produce a soaked feedstock; (ii) at least partially dewatering the soaked feedstock to produce a partially dewatered feedstock; (iii) pretreating the partially dewatered feedstock in the presence of sulfur dioxide, sulfurous acid or a combination thereof to produce a pretreated feedstock composition; (iv) feeding the pretreated feedstock composition to an enzymatic hydrolysis, wherein the concentration of dissolved solids in the pretreated feedstock composition fed to the enzymatic hydrolysis is at least about 50% of the concentration of dissolved solids in the pretreated feedstock composition produced in step (iii); (v) hydrolyzing the cellulose in the pretreated feedstock composition in the enzymatic hydrolysis with cellulose enzymes in the presence of said dissolved solids to produce glucose; and (vi) fermenting the glucose to produce the fermentation product.

According to one aspect of the invention there is provided a process for producing a fermentation product from a lignocellulosic feedstock comprising: (i) soaking the lignocellulosic feedstock in a liquid comprising water to produce a soaked feedstock; (ii) at least partially dewatering the soaked feedstock to produce an at least partially dewatered feedstock; (iii) feeding the at least partially dewatered feedstock to a heating device; (iv) adding steam and acid to the heating device, said steam heating the at least partially dewatered feedstock to a first temperature to provide a heated feedstock, said acid comprising at least one of sulfur dioxide and sulfurous acid; (v) pretreating the heated feedstock in the presence of the acid in a pretreatment reactor to produce a pretreated feedstock, said pretreatment reactor disposed downstream of said heating device; (vi) hydrolyzing cellulose in the pretreated feedstock with cellulose enzymes to produce glucose, wherein the concentration of dissolved solids in the pretreated feedstock fed to the hydrolysis is at least about 50% of the concentration of dissolved solids in the pretreated feedstock produced in step (v); and (vii) fermenting the glucose to produce the fermentation product.

According to one aspect of the invention there is provided a process for producing a fermentation product from a lignocellulosic feedstock comprising: (i) feeding the lignocellulosic feedstock to at least one soaking tank, wherein the lignocellulosic feedstock is soaked in a liquid comprising water to produce a soaked feedstock; (ii) feeding the soaked feedstock to a dewatering device, wherein the soaked feedstock is at least partially dewatered to produce an at least partially dewatered feedstock having a consistency between 15 wt % and 40 wt %; (iii) feeding the at least partially dewatered feedstock to a heating device, wherein the at least partially dewatered feedstock is fluffed-up as it is conveyed therethrough, and wherein steam and acid are added to the at least partially dewatered feedstock to produce an acidified feedstock having a pH between 0.5 and 2.5, said acid comprising at least one of sulfur dioxide and sulfurous acid, a residence time of the heating device less than 1 minute; (iv) feeding the acidified feedstock to at least one pretreatment reactor disposed downstream of the heating device, wherein the acidified feedstock resides for a time between 30 seconds and 30 minutes at a temperature between 170° C. and 230° C. to produce a pretreated feedstock; (v) feeding the pretreated feedstock to at least one hydrolysis tank, wherein cellulose in the pretreated feedstock is hydrolyzed with cellulase to produce glucose, a concentration of dissolved solids in the pretreated feedstock fed to the hydrolysis at least about 50% of a concentration of dissolved solids in the pretreated feedstock produced in step (iv); and (vi) feeding a stream comprising the glucose to at least one fermentation tank, wherein the glucose is fermented to produce the fermentation product.

According to another aspect of the invention there is provided a system for producing a fermentation product from a lignocellulosic feedstock comprising: at least one tank for soaking the lignocellulosic feedstock in at least one of water and an aqueous solution; a dewatering device disposed downstream of the at least one tank for at least partially dewatering the soaked feedstock to produce an at least partially dewatered feedstock; a heating device disposed downstream of the dewatering device for fluffing up the at least partially dewatered feedstock, said heating device having at least one inlet for introducing steam and an acid to the at least partially dewatered feedstock, said acid comprising at least one of sulfur dioxide and sulfurous acid; at least one pretreatment reactor disposed downstream of the heating device, said at least one pretreatment reactor including at least one outlet for discharging a pretreated feedstock; at least one hydrolysis tank disposed downstream of said at least one outlet for hydrolyzing cellulose in the pretreated feedstock with cellulase enzymes to produce glucose; at least one system disposed between the at least one outlet and the at least one hydrolysis tank, said at least one system including at least one of a cooling system, a pH adjustment system, a solid liquid separator, a washing system, and a dilution system, said at least one system feeding the pretreated feedstock to the at least one hydrolysis tank such that a concentration of dissolved solids in the pretreated feedstock fed to the hydrolysis is at least about 50% of the concentration of dissolved solids in the pretreated feedstock produced by the at least one pretreatment reactor; and at least one fermentation tank disposed downstream of the at least one pretreatment reactor for fermenting the glucose to produce the fermentation product.

According to embodiments of any of the foregoing aspects of the invention, the sulfur dioxide, sulfurous acid, or a combination thereof are added (i) to the aqueous solution used in soaking, (ii) prior to soaking, or (iii) a combination thereof, and sulfuric acid is added subsequent to the step of soaking. The sulfur dioxide, sulfurous acid, or a combination thereof, may be added to the aqueous solution used in soaking.

According to further embodiments of any of the foregoing aspects of the invention, the step of at least partially dewatering is conducted with a screw press.

According to embodiments of either of the above aspects of the invention, the inorganic alkali is added subsequent to pretreating and prior to enzymatic hydrolysis to increase the pH of the pretreated feedstock composition. The pH may be increased to between 4 and 7.5. The inorganic alkali may be calcium carbonate and/or potassium carbonate.

The lignocellulosic feedstock may be an agricultural residue, a biomass or energy crop, hardwood or a combination thereof. According to further embodiments, the lignocellulosic feedstock is an agricultural residue, or biomass crop or an energy crop.

In certain embodiments, the pretreating conducted in accordance with any of the foregoing aspects is at a temperature of between 170° C. and 230° C. The pH of the pretreating may be between 0.5 and 2.5. In further embodiments, the duration of the pretreating is from 10 seconds to 30 minutes.

In further embodiments of any of the foregoing aspects of the invention, at least 70% (w/w) of the concentration of dissolved solids in the pretreated feedstock composition are fed to the enzymatic hydrolysis. In further embodiments, at least 75% (w/w) of the concentration of dissolved solids in the pretreated feedstock composition are fed to the enzymatic hydrolysis.

According to further embodiments, between the steps of soaking and hydrolyzing, the undissolved solids content is between 15 wt % and 40 wt %, or between 15 wt % and 35 wt %.

In another embodiment of the invention, there is no solids-liquid separation between the steps of pretreating and hydrolyzing. In a further embodiment, the solids-liquid separation there is no washing carried out on the pretreated feedstock composition.

According to a further embodiment of any of the foregoing aspects of the invention, at least a portion of the aqueous solution from the step of soaking is removed during the dewatering and re-used in the process.

DETAILED DESCRIPTION

Feedstock

Figure 1:
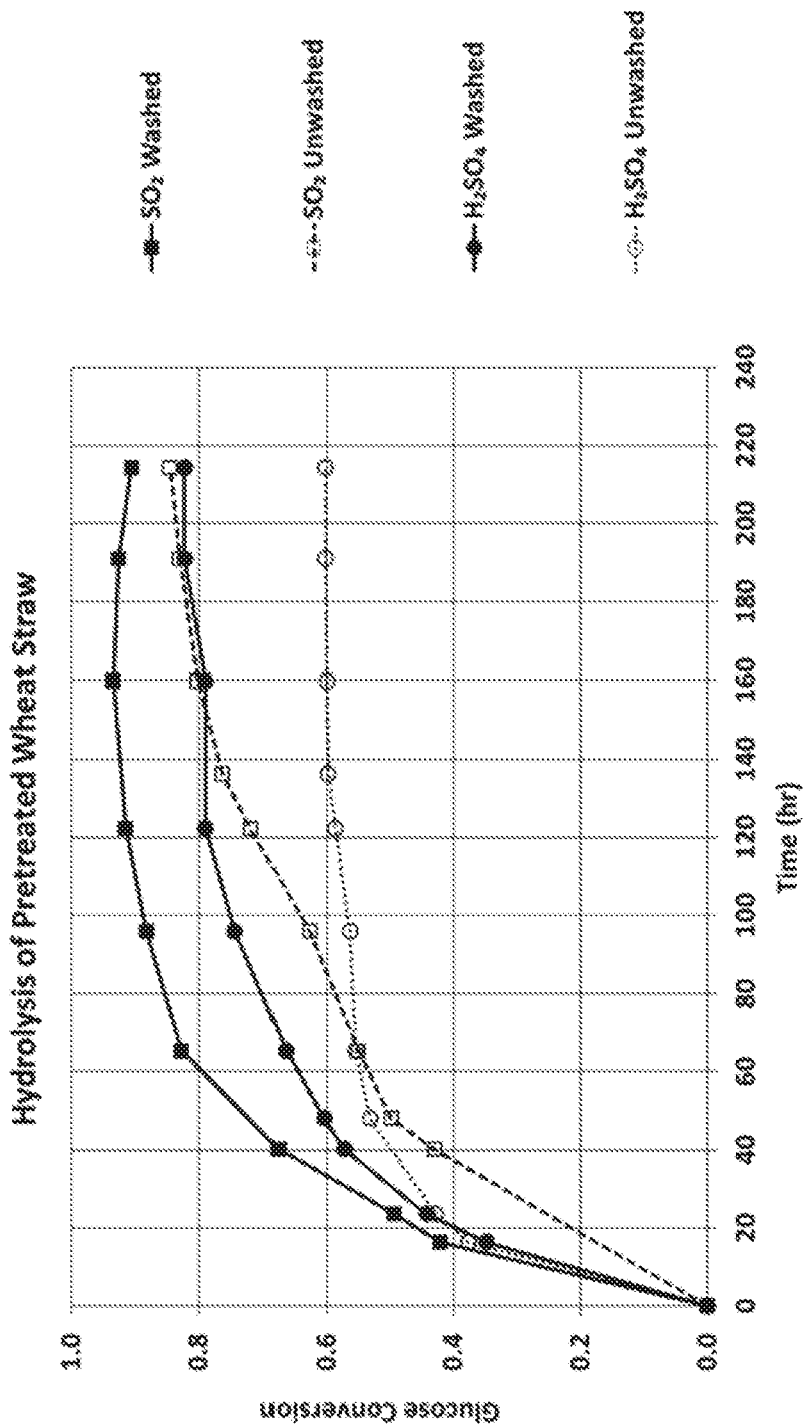
FIG. 1 is a plot of HPLC-measured glucose conversion as a function of hydrolysis time.

In one embodiment, the process utilizes a lignocellulosic feedstock. By the term "lignocellulosic feedstock", it is meant any type of woody or non-woody plant biomass or feedstock derived from plant biomass. The combined content of cellulose, hemicellulose and lignin in the lignocellulosic feedstock is typically greater than 25 wt % (w/w). Sucrose, fructose and starch can be present, hut typically in lesser amounts than cellulose and hemicellulose.

Examples of lignocellulosic feedstock are known to those skilled in the art and include: (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum (including sweet sorghum), cord grass, rye grass, miscanthus, reed canary grass, C3 grasses such as *Arundo donax*, or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber and corn cobs.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or fines.

Municipal waste includes post-consumer material or waste from a variety of sources such as domestic, commercial, institutional and/or industrial sources. For example, the term includes refuse from waste collection and/or sewage sludge.

Lignocellulosic feedstock can be a mixture of fibers that originate from different kinds of plant materials, including mixtures of cellulosic and non-cellulosic feedstocks. Moreover, new lignocellulosic feedstock varieties may be produced from any of those listed above by plant breeding or by genetic engineering.

In an embodiment of the invention, the lignocellulosic feedstock is (i) an energy or biomass crop, (ii) an agricultural residue and/or (iii) hardwood.

In a further embodiment of the invention, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In another embodiment of the invention, the lignocellulosic feedstock is a non-woody lignocellulosic feedstock such as (i) an energy crop, and/or (ii) an agricultural residue.

In another embodiment of the invention, the lignocellulosic feedstock is straw, stover or an energy crop. As used herein, straw refers to the stem, stalk and/or foliage portion of crops remaining after the removal of starch and/or sugar containing components for consumption. Examples of straw includes, but are not limited to sugar cane tops and/or leaves, oat straw, wheat straw, rye straw, oat straw, rice straw and barley straw. Stover includes the stalk and foliage portion of crops after the removal of starch and/or sugar containing components of plant material for consumption. Examples of stover include but are not limited to soybean stover, sorghum stover and corn stover.

Lignocellulosic feedstocks that have particle sizes of less than about 6 inches may not require size reduction. For feedstocks of larger particle sizes, the feedstock may be subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners, hydropulpers, and hydrapulpers. In one embodiment, at least 90% by volume of the particles produced from the size reduction may have a length less than between about $1/16$ and about 6 inches. Suitable equipment for the particle size reduction is a hammer mill, a refiner or a roll press as disclosed in WO 2006/026863.

The feedstock may be slurried in water prior to soaking. The production of an aqueous slurry may allow the feedstock to be pumped.

The lignocellulosic feedstock may also be leached prior to soaking as set forth in WO 02/070753 (Griffin, which is incorporated herein by reference). Removal of sand from the feedstock may also be carried out using wet or dry sand removal techniques that are known in the art. Examples include the use of a hydrocyclone or a sieve.

Soaking

The lignocellulosic feedstock is soaked in an aqueous solution prior to pretreating. The soaking can be conducted at any stage prior to pretreating. For example, the soaking can be conducted before, during, or subsequent to a size reduction step. The aqueous solution may include water optionally comprising one or more chemicals, such as a solution comprising pretreatment chemical. The solution may be a recycle stream obtained from other stages of the process. The soaking is typically conducted in a tank or other suitable equipment to handle soaked material. In one embodiment, soaking is achieved in a leaching step.

Soaking may be carried out in the presence of sulfur dioxide sulfurous acid. Sulfurous acid is the aqueous solution of sulfur dioxide. Soaking may also involve the addition of water (without acid). In this latter embodiment, the sulfur dioxide and/or sulfurous acid can be added to the feedstock downstream of soaking and prior to or during pretreating. For example, the sulfur dioxide and/or sulfurous acid can be added to a feedstock that has been at least partially dewatered.

The soaking is typically conducted at low consistency. Examples of consistency ranges at which the soaking can be conducted include between 1 and 20 wt % (wt:wt), or 2 and 18 wt % or between 3 and 15 wt % undissolved solids as determined by the method of Example 3. The soaking is carried out at 20° C. to 80° C. for about 1 to about 20 minutes, or more. It is carried out in one or more batch or continuous vessels, or a combination thereof. The vessels are mixed, unmixed, or a combination thereof.

Dewatering

Subsequent to soaking, the feedstock may be at least partially dewatered to increase the undissolved solids content relative to the soaked feedstock. That is, the feedstock is dewatered to increase the undissolved dry solids consistency within a desired range prior to further processing. The term dewatering refers to removing the aqueous solution introduced during the soaking step and includes the removal of water and/or a solution comprising sulfurous acid. The dewatering may involve removing the aqueous solution under pressure from the feedstock, or at atmospheric pressure, as discussed below. Dewatering may be particularly advantageous when the pretreatment includes heating the feedstock with steam since there will be less water to heat.

There are a variety of known devices that can be utilized to at least partially dewater the soaked feedstock. Examples include drainers, filtration devices, screens, plug formation devices, extruders or a combination thereof.

In certain embodiments, a plug formation device may be used to at least partially dewater the soaked feedstock and form a plug of material, although separate devices for dewatering and plug formation can be employed. Without being limiting, a plug formation device suitable for use in the invention is a pressurized screw press. Water separated from the lignocellulosic feedstock by the dewatering step may be reused in the process, such as for slurrying and/or soaking the incoming feedstock, as described previously.

Examples of plug formation devices include a pressurized screw press, a co-axial piston screw feeder, a modular screw device, or a plug screw feeder.

If the feedstock is subjected to dewatering under pressure, the pressure increase may be caused by one or more high pressure pumps. The pump or other feeding device increases the pressure of die feedstock prior to dewatering to e.g., about 45 psia to about 900 psia, or about 70 psia to about 800 psia or about 140 psia to about 800 psia. The pressure may be measured with a pressure sensor located at a feedstock inlet port on a dewatering device or a plug formation device that also dewaters the feedstock. Alternatively, the feedstock subjected to dewatering may be at atmospheric pressure or at a pressure below about 45 psia.

There my be an optional step of pre-draining the feedstock in order to drain out liquid from a feedstock at atmospheric pressure or higher. This pre-drained feedstock can then be subjected to further dewatering.

The consistency is higher after dewatering than prior to dewatering. The consistency can be readily selected by those of skill in the art. For example, the consistency targeted will often be high enough to generate the desired results in pretreatment and hydrolysis, but not so high as to create an at least partially dewatered feedstock that cannot be heated uniformly in the pretreatment reactor. The at least partially dewatered feedstock may have an undissolved solids content of between 18 wt % and 40 wt % or between 20 wt % and 35 wt % or between 22 wt % and 32 wt % or any value therebetween.

Heating Step

The feedstock may be heated during or prior to pretreatment. Without being limiting, the at least partially dewatered feedstock may be heated with steam. This may involve utilizing commercially available mixing devices designed for introducing steam and optionally sulfurous acid and/or sulfur dioxide. The acid may be introduced through one or more spray nozzles.

In one embodiment, the at least partially dewatered lignocellulosic feedstock is fed to a heating device, such as a heating chamber, in which the feedstock is treated with at least steam. Without being limiting, the feedstock may be broken up as it is conveyed through the heating chamber. The heating chamber may be a horizontally-oriented or essentially horizontally-oriented device. The feedstock may be heated by direct steam contact, which allows for efficient heat transfer.

In one embodiment, the heating device is disposed downstream of a plug formation device and/or a dewatering device that compresses the soaked lignocellulosic biomass to provide a compacted accumulation of biomass having a consistency between about 15 wt % and about 40 wt %. Advantageously, this consistency range has been found to provide a reasonable compromise between providing sufficient moisture for pretreatment, without overwhelming the system with excess water. In one embodiment, the heating device includes an elongated heating chamber having a rotatable shaft mounted coaxially therein, where the rotatable shaft has a plurality of elongated protrusions and/or paddles projecting therefrom. As the shaft rotates, the elongated protrusions and/or paddles fluff up the compacted accumulation of biomass, thereby increasing the volume occupied by the biomass and/or increasing the accessible surface area of the biomass. Advantageously, this fluffing action distributes the at least partially dewatered biomass over a more uniform area and/or makes it more permeable to steam, sulfur dioxide, and/or sulfurous acid. Accordingly, when steam and acid (e.g., sulfur dioxide and/or sulfurous acid) are injected into the heating chamber a more uniform distribution of the heat and acid may be achieved. Moreover, there is a more rapid heat transfer. Furthermore, since the biomass has been soaked and dewatered, and since the acid may be added as the shaft rotates, acid impregnation is more rapid than static systems that do not actively agitate and/or fluff the biomass during sulfur dioxide impregnation.

For example, in one embodiment, the heating device includes a horizontally-oriented or essentially horizontally-oriented elongate chamber having disintegrating elements for breaking up plugs, plug segments, and/or compact accumulations of biomass into the original particles/fibres (e.g., the compacted/compressed biomass (e.g., forming the plug) is fluffed up such that the particles thereof are separated and/or spread out with respect to volume). In this embodiment, the elongate chamber may include inlets for direct steam injection (e.g., to preheat the biomass and provide efficient heat transfer) and/or adding pretreatment chemicals (e.g., sulfur dioxide and/or sulfurous acid). In general, the inlet(s) for direct steam injection and acid injection may be different or the same (e.g., the steam and acid may be combined at a T junction before entering the heating device). In one embodiment, the inlets for direct steam injection and acid injection are different, and are disposed within a same region of the heating device (e.g., near the biomass inlet). In another embodiment, the inlets for direct steam injection and acid injection are different, and are disposed within different regions of the heating device (e.g., the steam injection inlet(s) are disposed near the biomass inlet, whereas the acid inlet(s) are disposed near the middle and/or biomass outlet end of the heating device).

In one embodiment, the heating device includes a heating chamber or a high shear heating chamber as described in US. Pat. Publication No. 2013/0071903, which is hereby incorporated by reference and particularly for the purpose of describing such heating chambers.

In one embodiment, the residence time in the heating device and/or heating chamber is between about 1 second and about 60 seconds. In one embodiment, the residence time is greater than 60 seconds. In one embodiment, the residence time is less than about 45 seconds. In one embodiment, the residence time is less than about 30 seconds. Providing a residence time that is less than about 1 minute is advantageous in that the amount of pretreatment that may occur in the heating device is reduced. In one embodiment, the residence time in the heating device and/or heating chamber is selected to be equal to or less than the time required to heat the lignocellulosic biomass to the pretreatment temperature. Advantageously, limiting the residence time in the heating chamber to about, or less than, the time required to heat the lignocellulosic biomass to the pretreatment temperature minimizes the amount of pretreatment occurring in the heating chamber.

In one embodiment, the residence time in the heating device and/or heating chamber is less than the total residence time in the pretreatment reactor(s). In one embodiment, the residence time in the heating device and/or heating chamber will be less than ½ the total residence time in the pretreatment reactor(s). In one embodiment, the residence time in the heating device and/or heating chamber will be less than ⅓ the total residence time in the pretreatment reactor(s). In one embodiment, the residence time in the heating device and/or heating chamber will be less than ¼ the total residence time in the pretreatment reactor(s).

In general, the residence time in the heating device and/or heating chamber will be selected to reduce and/or minimize hydrolysis of hemicellulose in the at least partially dewatered feedstock within the heating device/chamber. Accordingly, very little sugar (e.g., C5 and/or C6 sugars) will be produced in the heating chamber/device and transferred to the pretreatment reactor, where the sugar may be degraded and/or converted to potential inhibitors.

The at least partially dewatered feedstock need not be fed directly into a heating device. Any of a variety of known devices may be positioned between a dewatering device and the heating device. Without being limiting, examples of such devices include mechanical restricting devices, restraining devices, scrapers and conveyors. It should be understood that the plug may break into segments as it is discharged from the plug formation device, or into other devices positioned downstream of the plug formation device, or as it is fed into the heating chamber.

Pretreatment

During pretreatment, the lignocellulosic feedstock is contacted with at least sulfur dioxide, sulfurous acid or a combination thereof. As mentioned, the sulfur dioxide, sulfurous acid, or a combination thereof, may be introduced or added at any stage upstream of pretreatment, including during soaking or upstream of soaking, or during the pretreating step itself. The feedstock may be contacted with sulfur dioxide gas and/or an aqueous solution comprising sulfurous acid. Sulfurous acid may be produced upon the addition of sulfur dioxide to an aqueous solution. As described previously, the feedstock may be soaked in an aqueous solution comprising sulfurous acid and subsequently subjected to elevated temperature to pretreat the feedstock or soaking can be conducted with water and the acid can be added downstream of soaking, but prior to or during pretreating.

The pretreatment may additionally comprise contacting the feedstock with other acids or chemicals besides sulfurous acid and/or sulfur dioxide if desired. For example, sulfur dioxide and/or sulfurous acid can be added to the feedstock during soaking or upstream of soaking. During or after soaking, sulfuric acid may be added to the dewatered feedstock. Addition of the acids in this manner can improve the economics of the process. In another example, the pretreatment may also be conducted in the presence of up to 50 g/L ethanol that is recycled from downstream in the process, for example so as to reduce the energy usage in the process.

The pretreatment is generally conducted so as to disrupt the fiber structure of the lignocellulosic feedstock and increase its surface area to make it accessible to cellulase enzymes. The pretreatment may be performed no that a certain degree of xylan hydrolysis is achieved and only a small amount of conversion of cellulose to glucose occurs. The pretreatment is conducted by lowering the pH and increasing the temperature of the lignocellulosic feedstock.

The pretreatment may be conducted to achieve a pH between about 0.5 and about 3.0 or between about 0.5 and about 2.5. The pH is measured by taking a sample of a feedstock composition after the addition of acid is complete, and measuring the pH at ambient temperature. If the acid is added prior to pretreatment, the pH is measured on a sample prior to pretreatment. If the acid is added during pretreatment, the pH is measured on a sample after pretreatment.

Without being limiting, the pretreatment may be carried out at a maximum temperature of about 170° C. to about 230° C. However, in practice, there will be a time delay in the pretreatment process before the feedstock reaches this temperature range. The above temperatures correspond to those values reached after sufficient application of heat to reach a temperature within this range. The time that the feedstock is held at this temperature may be about 10 seconds to about 30 minutes, or any range therebetween. After this pretreatment time has been achieved, the pretreated material is discharged from the pretreatment reactor. The pressure is decreased to atmospheric, such as by carrying out one or more flashes. At the conclusion of the pretreatment, the pressure is lowered, such as to atmospheric, and the temperature is brought to below 100° C. to produce the pretreated feedstock composition. An example of a suitable pretreatment system for use in the invention is disclosed in WO 2010/022511.

The pretreated feedstock composition will comprise dissolved solids. The dissolved solids are measured as set forth in Example 5. Generally, the methodology involves filtering the pretreated feedstock composition, collecting the filtrate, and drying the filtrate. Examples of dissolved solids include xylose, glucose, and arabinose sugar, organic acids including acetic acid and glucuronic acid, soluble products of reactions between sulfurous acid and lignin, such as sulfonic acids and lignosulfonic acids, soluble degradation products, and/or one or more salts, such as sulfite salts. The soluble degradation products include phenolic compounds, such as low molecular weight phenolics, including phenolic lignin, and furans such as furfural and hydroxymethylfurfural (HMF).

Subsequent to pretreatment, the pH of the acidic pretreated feedstock composition is adjusted to a pH at which enzymatic hydrolysis can be conducted. This is a pH value that is suitable for the enzymatic hydrolysis reaction. The pH may be adjusted to between 4 and 7 or more typically between about 4 and about 7.5 or between about 4 and about 7.0, or between about 4 and about 6.5 or between about 4 and about 6. According to further embodiments, the pH is adjusted so that it is less than 8 and is at a value that is compatible with cellulase enzymes. The pH at which a cellulase enzyme is compatible depends on the particular enzyme utilized in the cellulose hydrolysis, but can be determined readily by those of skill in the art.

The pH adjustment is most advantageously carried out with an inorganic alkali. The term denotes that both the cation and anion in the alkali compound are inorganic. Any suitable inorganic alkali, or mixtures thereof, can be utilized in accordance with the invention. Non-limiting examples are the cations, potassium, sodium, ammonium and calcium, and the anions, carbonate and hydroxyl. Ammonia gas is also a suitable inorganic alkali. Preferably, the inorganic alkali may be a carbonate salt. Examples of suitable carbonate salts include calcium carbonate, potassium carbonate or mixtures thereof. According to certain embodiments of the invention, the inorganic alkali improves the enzymatic hydrolysis of the cellulose with cellulase relative to a pH adjustment carried out with an organic alkali such as sodium acetate or sodium citrate conducted under otherwise identical conditions.

According to further embodiments of the invention, alkali is not added to the aqueous pretreated feedstock composition prior to enzymatic hydrolysis and after pretreatment to achieve a pH of 8 or greater.

An inorganic alkali can be added to the pretreated feedstock composition after it is cooled, before cooling, or at points both before and after cooling. The point of alkali addition can coincide with the cellulase enzyme addition, or the addition point can be upstream or downstream of the location of the enzyme addition. If the enzyme is added upstream of the alkali addition point, the contact time of the enzyme at the lower pH of the pretreated feedstock composition would typically be minimized to avoid enzyme inactivation. The alkali may be added prior to enzyme addition or simultaneously therewith.

As set forth above, according to one embodiment of the invention, the pretreated feedstock composition is fed to an enzymatic hydrolysis, wherein the concentration of dissolved solids fed to the enzymatic hydrolysis is least 50% (w/w) of the concentration of dissolved solids in the pretreated feedstock composition. In further embodiments of the invention, a concentration of at least 55% (wlv), at least 60% (w/w), at least 65% (w/w), at least 70% (w/w), at least 75% (w/w), at least 80% (w/w), at least 85% (w/w) or at least 90% (w/w) of the concentration of dissolved solids in the pretreated feedstock composition are fed to the enzymatic hydrolysis. There is therefore little washing or dilution of the pretreated feedstock composition prior to the enzymatic hydrolysis. According to one embodiment of the invention, there is no washing of the pretreated feedstock composition prior to enzymatic hydrolysis.

According to a further embodiment of the invention, the process steps carried out between pretreating and enzymatic hydrolysis may "consist essentially of" cooling and adjusting the pH of the pretreated feedstock composition. By this it is meant that additional steps may be included between pretreating and hydrolysis of cellulose with cellulose enzymes besides cooling and pH adjustment that do not materially increase water usage in the process. Without being limiting, this may include steps such as centrifuging and/or pressing of the pretreated feedstock composition. A pressing of the solids or a small amount of washing and/or dilution may be conducted, consistent with maintaining greater than 50% concentration of dissolved solids, or greater than 70%, but not necessarily 100% concentration of dissolved solids. Examples of cooling include exposing the pretreated feedstock composition to one or more heat exchangers to cool it from the final pretreatment temperature to the temperature at which enzymatic hydrolysis is carried out.

In addition to dissolved solids, the pretreated feedstock composition comprises insoluble solids such as cellulose and lignin. The lignin may comprise both native and sulfonated lignin.

The pretreated feedstock composition is subsequently fed to enzymatic hydrolysis with cellulose enzymes in order to convert the cellulose to glucose. The enzymatic hydrolysis of cellulose using cellulose enzymes is described in more detail below.

Enzymatic Hydrolysis

Subsequent to pH adjustment with the inorganic alkali, the cellulose is hydrolyzed to glucose in a subsequent step that uses cellulase enzymes. The enzymatic hydrolysis of the cellulose to soluble sugars can be carried out with any type of cellulase enzymes suitable for such purpose and effective at the pH and other conditions utilized, regardless of their source. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens* (see Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12).

In addition CBH, EG and beta-glucosidase, there are several accessory enzymes that aid in the enzymatic digestion of cellulose (see WO 2009/026722 (Scott), which is incorporated herein by reference and Harris et al., 2010, Biochemistry, 49:3305-3316). These include EGIV, also known as glycoside hydrolase 61, swollenin, expansin, lucinen and cellulose-induced protein (Cip). Glucose can be enzymatically converted to the dimers gentiobiose, sophorose, laminaribiose and others by beta-glucosidase via transglycosylation reactions.

In general, the enzyme dosage may be measured in milligrams (mg) protein per gram of cellulose or in Filter Paper Units (FPU or IU) per grain of cellulose. The FPU is a standard measurement familiar to those skilled in the art and is defined and measured according to Ghose (Pure and Appl. Chem., 1987, 59:257-268). For example, in one embodiment, the cellulase dosage is between about 1.0 and about 40.0 FPU per gram of cellulose. In one embodiment, the cellulase dosage is between about 10 to 20 FPU per gram cellulose. Preferably, the enzyme dosage is measured in milligrams protein per gram cellulose. For example, in one embodiment, the cellulase dosage is between about 2 to 20 mg protein per gram cellulose.

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC #3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. It is also contemplated that the β-glucosidase enzyme may be modified to include a cellulose binding domain, thereby allowing this enzyme to bind to cellulose.

As would be appreciated by those of skill in the art, the temperature of the pretreated feedstock composition may be adjusted so that it is within the optimum range for the activity of the cellulose enzymes. Generally, a temperature of about 45° C. to about 70° C., or about 45° C. to about 65° C., or any temperature therebetween, is suitable for most cellulase enzymes. However, the temperature of the pretreated feedstock composition may be higher for thermophilic cellulase enzymes. The duration of the enzymatic hydrolysis may be from 12 to 200 hours or any range therebetween. Preferably, the hydrolysis is carried out at an initial solids concentration of 10% to 40%, or 15% to 35% UDS, or 18% to 30% UDS, or 20% to 30% UDS as measured by the method of Example 3.

The enzymatic hydrolysis and fermentation may be conducted in separate vessels so that each biological reaction can occur at its respective optimal temperature. However, the hydrolysis may be conducted simultaneously with fermentation in a simultaneous saccharification and fermentation (SSF). SSF is typically carried out at temperatures of 35-38° C., which is a compromise between the 50° C. optimum for cellulose and the 28° C. optimum for yeast.

Fermentation

Fermentation of glucose resulting from the hydrolysis may produce one or more of the fermentation products selected from an alcohol, a sugar alcohol, an organic acid and a combination thereof.

The fermentation may be conducted at a pH between about 4.0 and about 6.0, or between about 4.5 and about 6.0. To attain the foregoing pH range for fermentation, it may be necessary to add alkali to the stream comprising glucose.

In one embodiment of the invention, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (e.g., U.S. Pat. Nos. 5,789,210, 5,866,382, 6,582,944 and 7,527,927 and European Patent No. 450530) or (b) fungal or bacterial xylose isomerase (XI) gene (e.g., U.S. Pat. Nos. 6,475,768 and 7,622,284). Examples of yeasts that have been genetically modified to ferment L-arabinose include, but are not limited to, recombinant *Saccharomyces* strains into which genes from either fungal (e.g., U.S. Pat. No. 7,527,951) or bacterial (e.g., WO 2008/041840) arabinose metabolic pathways have been inserted.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation product is recovered, meaning that it is concentrated and/or purified from a fermented solution. A remaining stream contains components besides the fermentation product remaining after the recovery. Non-limiting examples of such components include inorganic salts, unfermented sugars and organic salts.

If ethanol or butanol is the fermentation product, the recovery is carried out by distillation, typically with further concentration by molecular sieves or membrane extraction.

The fermentation broth that is sent to distillation is a dilute alcohol solution containing solids, including unconverted cellulose, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is typically operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

A still bottoms stream remaining after ethanol distillation and containing solids is withdrawn from the bottom of one or more of the column(s) of the distillation unit. The still bottoms stream will typically comprise inorganic salts, unfermented sugars, and organic salts.

When the alcohol has a higher boiling point than water, such as butanol, the distillation is run to remove the water and other volatile compounds from the alcohol. The water vapor exits the top of the distillation column and is known as the "overhead stream".

As discussed above, soaking the lignocellulosic feedstock, dewatering the soaked feedstock, and pretreating the soaked and dewatered feedstock in the presence of sulfurous acid and/or sulfur dioxide is advantageous with regard to providing a relatively efficient pretreatment that may provide fewer and/or lower concentrations of contaminants, inhibitors, and/or inactivators for hydrolysis.

Laboratory experiments have been carried out to validate soaking, dewatering, and pretreating in the presence of $SO_2$, by pretreating lignocellulosic biomass with sulfurous acid at a relatively high consistency (e.g., 30 wt %). In fact, it has been found that pretreating lignocellulosic feedstock in the presence of sulfurous acid and/or sulfur dioxide produces less and/or fewer inactivating compounds for hydrolysis than conventional pretreatment with sulfuric acid. For example, it has been found that the difference in glucose conversion between washed and unwashed samples prepared by $SO_2$-catalyzed pretreatment is significantly less than the difference in glucose conversion between washed and unwashed samples prepared by $H_2SO_4$-catalyzed pretreatment. Moreover, it has been found that the glucose conversion plateaus faster for the hydrolysis of $H_2SO_4$-catalyzed pretreated material than for $SO_2$-catalyzed pretreated material, thus indicating the presence of inactivating compounds. For example, see the Examples and FIG. 1.

While the $SO_2$ pretreatment conditions disclosed in the Examples may result in fewer inactivating compounds, further advantages arise from soaking and/or dewatering. For example, contacting the lignocellulosic feedstock with sulfurous acid, and/or soaking the lignocellulosic feedstock in an aqueous solution followed dewatering and contact with sulfur dioxide, may provide a more uniform sulfur dioxide distribution. Providing a more uniform sulfur dioxide distribution may result in a more uniform cook in the pretreatment, which may further reduce the number of inhibitors/inactivators. Dewatering reduces the amount of water present in pretreatment, provides for faster, more efficient steam heating in pretreatment, and/or also may provide a more uniform cook. Advantageously, providing a pretreatment that produces fewer contaminates, inhibitors, and/or inactivators for hydrolysis, may allow the pretreated material to be fed to hydrolysis with little or no washing.

Although soaking does use additional water, it may be easier to remove and/or recycle the soaking water, than it would be to remove and/or recycle water used for washing pretreated material. In particular, the muddy texture of pretreated lignocellulosic feedstock may provide challenges in terms of filtering (e.g., compared to the fibrous texture of the untreated lignocellulosic feedstock).

Accordingly, significant economic advantages related to soaking, dewatering, and pretreating in the presence of sulfurous acid/sulfur dioxide are provided. For example, soaking equipment is less expensive than washing equipment.

EXAMPLES

Example 1

$SO_2$ Catalyzed Pretreatment of Lignocellulosic Material

An $SO_2$ catalyzed batch pretreatment of wheat straw was conducted in 25 mL, stainless steel, laboratory tubular reactors (i.e., about 5 inches in length). The wheat straw was hammer-milled to provide an average particle size of ¼ inch-1 inch (0.635-2.54 cm) and had a cellulose/glucan content of 34.61%, xylan content of 20.09%, a lignin content of 20.49% and a total solids (TS) content of 93.25%, w/w on a dry basis. The carbohydrate assay was based on Determination of Structural Carbohydrates and Lignin in Biomass-LAP (Technical Report NREL/TP-510-42618).

Each tubular reactor was charged with approximately 1.646 g of accurately weighed wheat straw and 3.47 mL of sulfurous acid solution (≥6% $H_2SO_3$, from Sigma-Aldrich), thus providing a slurry having a consistency of about 30 wt % and a pH of 1.1. Each tubular reactor was repeatedly shaken/inverted such that the wheat straw was soaked in the sulfurous acid for at least 1 minute, and then placed in an oil bath preheated to 195° C. The tubular reactor remained immersed in the oil bath for 5 minutes. At the end of the 5 minute pretreatment time, the tubular reactor was removed from the oil bath and placed in an ice bath for 5 minutes. The contents of the tubular reactors (e.g., pretreated material) were removed, weighed, and combined in a sealable plastic bag.

A portion of the pretreated material was removed for washing, to prepare a washed pretreatment sample for hydrolysis. Another portion of the pretreated material was removed to prepare an unwashed pretreatment sample for hydrolysis. The washed and unwashed samples were subject to enzymatic hydrolysis on the same day as the pretreatment.

A portion of the pretreated material was reserved to determine the undissolved solids (UDS) concentration, total solids (TS) concentration, dissolved solids (DS) concentration, and/or the concentration of monomeric sugars and/or degradation products.

More specifically, the filtrate from a portion of the $SO_2$ pretreated material was found to contain 9.77 g/L glucose, 75.42 g/L xylose, 0.21 g/L HMF and 4.36 g/L of furfural, using the method described in Example 6.

The carbohydrate content of the $SO_2$ pretreated material was ascertained with a carbohydrate assay based on Determination of Structural Carbohydrates and Lignin in Biomass-LAP (Technical Report NREL/TP-510-42618). The $SO_2$ pretreated material was found to contain 57.84% cellulose, 1.61% xylan and 27.88% insoluble lignin, w/w on a dry basis.

All experiments conducted with or based on $SO_2$/sulfurous acid are carried out in a fume hood, including the drying of samples for determining the dissolved solids and total solids concentrations.

Example 2

$H_2SO_4$ Catalyzed Pretreatment of Lignocellulosic Material

A $H_2SO_4$ catalyzed batch pretreatment of wheat straw was conducted in a 97 L steam gun, for comparison with the $SO_2$-catalyzed pretreatment. The wheat straw was hammer-milled to provide an average particle size of about ¼ inch-1 inch (0.635-2.54 cm) and had a cellulose/glucan content of 34.61%, a xylan content of 20.09%, a lignin content of 20.49%, and a total solids content of 89.5%, w/w on a dry basis.

To prepare for pretreatment, 400 g of the wheat straw was soaked overnight in a solution prepared from 22.3 mL of 96.5% $H_2SO_4$ and 6.72 L of water, thus providing a slurry having a consistency of about 5% and a pH of 1.30. Excess $H_2SO_4$ solution was drained from the wheat straw, which was then placed in a Bock basket centrifuge for 30 seconds. The centrifuged, $H_2SO_4$ soaked, lignocellulosic feedstock, which had a total solids (TS) concentration of 29.18%, was then stored at about 4° C.

The steam gun, which was preheated to 200° C., was charged with 1000 g of the centrifuged, $H_2SO_4$ soaked straw, which was cooked for 2 minutes. After 2 minutes, the steam gun was depressurized to 5 psi and the pretreated straw was removed from the steam gun. The pretreated material, which weighed 948.5 g and had a UDS of 19.63 wt %, was cooled before storage at about 4° C.

A portion of the pretreated material was removed for washing, to prepare a washed pretreatment sample for hydrolysis. Another portion of the pretreated material was removed to prepare an unwashed pretreatment sample for hydrolysis.

A portion of the pretreated material was reserved to determine the undissolved solids (UDS) concentration, total solids (TS) concentration, dissolved solids (DS) concentration, and/or the concentration of monomeric sugars and/or degradation products.

More specifically, the filtrate from a portion of the $H_2SO_4$ pretreated material contained 17.54 g/L glucose, 63.42 g/L xylose, 0.45 g/L HMF and 1.89 g/L of furfural.

The carbohydrate content of the $H_2SO_4$ pretreated material was ascertained with the carbohydrate assay as described above. The $H_2SO_4$ pretreated material was found to contain 54.33% cellulose, 1.40% xylan, and 29.72% insoluble lignin.

Example 3

Determination of Undissolved Solids Concentration

The determination of the undissolved solids (UDS) content, also referred to as the consistency, is carried out as follows. A fixed amount of a sample containing undissolved solids is dispensed into a plastic weigh dish and the weight is recorded accurately using an analytical scale. A glass microfiber filter paper circle of pore size 1.6 microns, appropriately sized for a Buchner funnel, is placed in an aluminum weighing tin and the combined weight of the tin and filter paper is recorded. After transferring the pre-weighed filter paper to the Buchner funnel, the pre-weighed sample is passed through the filter paper to isolate the solids. Small volumes of de-Ionized water are used to ensure that the solids are quantitatively transferred from the weigh dish to the Buchner funnel. The solids are then washed using excess deionized water, after which the washed sample and filter paper are transferred into the pre-weighed aluminum tin. Care should be taken to ensure the solids are quantitatively transferred. After drying the aluminum tin in a 105° C. oven overnight, the contents are weighed accurately and the UDS is quantified by determining, as a percent, the number of grams of dry solids per gram of sample. UDS measurements are performed in duplicate and averaged.

UDS measurements are performed on unwashed pretreated samples to determine the amount of pretreated sample to add to the hydrolysis flask (e.g., using about 0.5 g aliquots).

Example 4

Measurement of Total Solids Concentration in a Pretreated Feedstock Composition

The determination of the total solids (TS) content is carried out as follows. A fixed amount of a sample is dispensed into a pre-weighed aluminum tin (if sample is washed) or crucible (if sample is unwashed). After drying the aluminum tin/crucible in a 105° C. oven or muffle furnace (disposed in a fume hood) overnight, the contents are weighed accurately and the total solids are quantified by determining, as a percent, the number of grams of dry solids per gram of sample. TS measurements are performed in duplicate and averaged.

TS measurements are performed on washed pretreated samples to determine the amount of pretreated sample to add to the hydrolysis flask (e.g., using about 0.5 g aliquots).

Example 5

Measurement of Dissolved Solids Concentration in a Pretreated Feedstock Composition The determination of the dissolved solids concentration of a pretreated feedstock composition is carried out as follows. A glass microfiber filter paper circle of pore size 1.6 microns that has not been pre-wetted is placed in a Buchner funnel. A sample of a pretreated feedstock composition is applied to the filter paper and filtered by vacuum. The filtrate is collected and weighed into a pre-weighed crucible. After drying the crucible in a 105° C. muffle furnace (placed in a fume hood) overnight, the contents are weighed accurately and the concentration of dissolved solids is quantified by determining, as a percent, the number of grams of dry solids per gram of filtrate.

Alternatively, the concentration of dissolved solids (% DS) is obtained from

% DS=% TS−% UDS.

Example 6

Determination of the Concentration of Monomeric Sugars and/or Degradation Products Determination of the concentration of monomeric sugars and/or degradation products, such as furans, was achieved using high performance liquid chromatography (HPLC).

The sugar composition (e.g., concentration of glucose and/or xylose) of pretreated material and/or of aliquots from the enzymatic hydrolysis was determined using a Dionex ICS-3000 ion chromatography system equipped with an electrochemical detector (ED40) with gold electrode. Separation was performed on a CarboPac™ PA1 column (4×250 mm) and a PA1 guard column (4×50 mm) The detector temperature and column temperature were both 30° C. NaOH (10 and 200 mM solutions) was used as an eluent at a flow rate of 1.5 mL/min. All sample injection volumes were 25 μL. Sugar concentrations were calculated by comparison to standard sugar samples containing arabinose, galactose, glucose, xylose and cellobiose (Certified from Absolute Standards).

Concentration of furans (e.g., concentration of 5-(hydroxymethyl)furfural (HMF) and/or furfural) in the pretreated material and/or in aliquots from the enzymatic hydrolysis were determined using a Dionex ICS-3000 ion chromatography system equipped with a Dionex AD25 Absorbance detector set at 278 nm. Separation was performed on a Varian Microsorb-MV C18 (4×250 mm) and Phenomenex Security guard column with Carbo-H cartridges. Detector temperature and column temperature were both 30° C. A solution of 5:95 (v/v) ACN:deionized water was used as an eluent at a flow rate of 1 mL/min. All sample injection volumes were 25 μL. Furan concentrations were calculated by comparison to standard furan samples containing 5-(hydroxymethyl)furfural (HMF), furfuryl alcohol, and furfural (Certified from Absolute Standards).

The filtrate from a portion of the $SO_2$ pretreated material was found to contain 9.77 g/L glucose, 75.42 g/L xylose, 0.21 g/L HMF, and 4.36 g/L of furfural.

The filtrate from a portion of the $H_2SO_4$ pretreated material was found to contain 17.54 g/L glucose, 63.42 g/L xylose, 0.45 g/L HMF, and 1.89 g/L of furfural.

Example 7

Preparation of the Washed Pretreatment Samples for Hydrolysis

Washed pretreatment samples were prepared by suspending a portion of pretreated sample in ultra-purified water (Milli-Q™) in an approximately 1:1 (v/v) ratio, filtering the suspension through glass fiber filter paper (G6, 1.6 microns), and then repeating the alternating steps of adding the same volume of ultra-purified water (Milli-Q™) to the pretreated solids followed by filtration through the glass fiber filter paper, another eight times.

The washed pretreatment solids were added to a pre-weighed 50 mL Erlenmeyer flask, in an amount selected to provide a consistency of about 10 wt % for hydrolysis (e.g., corresponding to about 1 g of dry pretreated material for a total weight of the flask contents, including the enzyme, of 10 g). To determine the amount of wet, washed pretreatment solids that corresponds to 1 g of dry pretreatment material, 1 g is divided by the total solids (TS) of the washed pretreated sample.

In the washed $SO_2$ catalyzed pretreatment samples prepared according to Examples 1 and 7, the TS was found to be 21.43%, thus providing a target weight of wet slurry to be added to the Erlenmeyer flask of 4.6662 g.

Once an accurately weighed amount of washed pretreatment solids (target weight of 4.6662 g) has been added to the Erlenmeyer, 0.420 mL of 2.38 M sodium citrate buffer (prepared by adjusting the pH of citric acid monohydrate to about 5.2 with 30% NaOH) was added to the flask (e.g., an amount selected to provide a target 100 mM concentration once enzyme). Ultra-purified water (Milli-Q™) was then added to bring the flask contents up to a target weight, predetermined to bring the final weight of the contents to 10 g once enzyme is added. The flasks were incubated at 52° C., with moderate shaking at about 250 rpm, for 30 minutes to equilibrate substrate temperature.

Example 8

Preparation of the Unwashed Pretreatment Samples for Hydrolysis

Unwashed pretreatment samples were prepared by adjusting the pH of a portion of the as-is pretreated material to about 5 by adding a solution of 30% lime $(Ca(OH)_2)$ in small increments. The pH-adjusted pretreatment material was then added to a pre-weighed 50 mL Erlenmeyer flask, in an amount selected to provide a consistency of about 10 wt % for hydrolysis (e.g., corresponding to about 1 g of dry pretreated material for a total weight of the flask contents, including the enzyme, of 10 g). To determine the amount of pretreated slurry that corresponds to 1 g of dry pretreatment material, 1 g is divided by the UDS of the pH adjusted pretreated sample.

In the unwashed catalyzed pretreatment samples prepared according to Example 1, the UDS of the pH-adjusted pretreated sample was found to be 17.42%, thus providing a target weight of wet slurry to be added to the Erlenmeyer flask of 5.7389 g.

Once an accurately weighed amount of unwashed slurry (target weight of 53389 g) has been added to the Erlenmeyer, 0.420 mL of 2.38 M sodium citrate buffer (prepared by adjusting the pH of citric acid monohydrate to about 5.2 with 30% NaOH) was added to the flask (e.g., an amount selected to provide a target 100 mM concentration once enzyme). Ultra-purified water (Milli-Q™) was then added to bring the flask contents up to a target weight, predetermined to bring the final weight of the contents to 10 g once enzyme is added. The flasks were incubated at 52° C., in an orbital shaker (250 rpm), for 30 minutes to equilibrate substrate temperature.

Example 9

Enzymatic Hydrolysis of Pretreated Samples

Hydrolysis was initiated by adding liquid cellulase enzyme to the Erlenmeyer flasks prepared in Examples 7 and 8 (i.e., containing the pretreated material, citrate buffer, and make-up water), thus bringing the total content weight up to 10 g. Enzyme was added at 5 mg/g, 7 mg/g, and 9 mg/g (i.e., mg protein/g of cellulose enzyme loading). The flasks were incubated at 52° C. in an orbital shaker (250 rpm) for 215 hours.

The pH of the washed samples were maintained at about 5 (e.g., between 4.8 and 5.2) for the duration of the hydrolysis by the citrate buffer. The pH of the unwashed samples were periodically adjusted to 5 (i.e., twice a day for the first 72 hours of hydrolysis, and once a day for the remaining duration of the hydrolysis). The pH was adjusted by adding a solution of 30% lime $(Ca(OH)_2)$ in 10 µL increments. The volume of pH adjusting solution added was recorded, and used to adjust total volume when calculating cellulose conversion.

The hydrolyses were followed by measuring the sugar monomers in the hydrolysate. More specifically, aliquots obtained at 16, 24, 40, 48, 60, and 72 hours of hydrolysis, and at 24 hours intervals after the 72 hours, were used to analyze the sugar content. Each aliquot was obtained at the specific time interval by swirling the flask, withdrawing 200 µL of the flask contents with a wide-bore pipette tip and depositing it in a 1.5 mL Eppendorf centrifuge tube, placing the centrifuge tube in a boiling water for 10 minutes to deactivate the enzyme, and storing the aliquot at about 4° C. for subsequent sugar analysis.

To assay samples for monomeric sugars, the samples were warmed to room temperature and were centrifuged for 4 minutes at 14,800 rpm. The supernatant was diluted in water for measuring the glucose with the HPLC, and were measured using the method in Example 6.

Since the slurries in the hydrolysis flasks were too thick at time 0 hours, the glucose measurements at time 0 hours was calculated using the glucose concentration measured for the corresponding filtrate, the enzyme solution glucose contribution, and the total volume of the contents of the corresponding hydrolysis flask, which includes volume added from the lime addition, buffer solution, make-up water, and enzyme addition.

The glucose conversion was determined assuming:

$$\text{Maximum glucose} = \frac{\left(\begin{array}{c}\text{g of dry substrate} \times \\ \text{\% cellulose in the substrate}\end{array}\right)}{\text{aqueous volume(L)}} \times 2 \frac{(180.1559 \text{ g/mol})}{(324.28 \text{ g/mol})}$$

$$\text{Glucose conversion} = \text{concentration of glucose in aliquot/maximum glucose}$$

The results are presented in FIG. 1. More specifically, FIG. 1 shows a plot of glucose conversion as a function of time for both washed and unwashed samples, for both $SO_2$ and $H_2SO_4$ catalyzed pretreatments, with a 5 mg/g enzyme loading.

Referring to the assays referred to in Examples 1 and 2, the $SO_2$ catalyzed pretreatment resulted in more cellulose (e.g., 57.84% compared to 54.22%), more xylan (1.61% compared to 1.40%), and less insoluble lignin (e.g., 27.88% compared to 29.72%), relative to the $H_2SO_4$ catalyzed pretreatment. In addition, the filtrate from the $SO_2$ catalyzed pretreatment resulted in less glucose (9.77 g/L compared to 17.54 gL), more xylose (75.42 g/L compared to 63.42 g/L), less HMF (0.21 g/L compared to 0.45 g/L), and more furfural (4.36 g/L compared to 1.89 g/L), relative to the $H_2SO_4$ catalyzed pretreatment.

Referring to FIG. 1, hydrolysis of the $SO_2$ catalyzed pretreatment washed sample reached about 0.9 glucose conversion at 160 hours, whereas hydrolysis of the $H_2SO_4$ catalyzed pretreatment washed sample only reached 0.8 glucose conversion at 160 hours. By comparison, hydrolysis of the $SO_2$ catalyzed pretreatment unwashed sample reached 0.8 glucose conversion at 160 hours, whereas hydrolysis of the $H_2SO_4$ catalyzed pretreatment unwashed sample only reached 0.6 glucose conversion at 160 hours.

Although the hydrolysis of each washed pretreated material was generally more efficient than the hydrolysis of the corresponding unwashed pretreated material, the surprising result is that the hydrolysis of the unwashed $SO_2$ catalyzed pretreatment material (e.g., having a dissolved solids concentration that was approximately 54.4% (e.g. greater than about 50%) of the concentration of dissolved solids in the pretreated feedstock composition) reached substantially the same, or higher, glucose conversion as the hydrolysis of the washed $H_2SO_4$ catalyzed pretreatment material at times over 160 hours. In particular, even though the hydrolysis of the unwashed $SO_2$ catalyzed pretreatment material started out relatively slowly (e.g., even slow relative to the hydrolysis of the unwashed $H_2SO_4$ catalyzed pretreatment material), with time it eventually surpassed the glucose conversion obtained by hydrolysis of the washed $H_2SO_4$ catalyzed pretreatment material. Accordingly, without being bound by theory, it does not appear that there is a high concentration of inactivating compounds in the unwashed $SO_2$ catalyzed pretreatment material (e.g., for comparison, the hydrolysis of the $H_2SO_4$ catalyzed pretreatment material plateaus around 0.6, thus indicating at least some inactivation of the enzyme).

Advantageously, since the hydrolysis of the unwashed $SO_2$ catalyzed pretreatment material reached substantially the same, or a higher, glucose conversion as the hydrolysis of the washed $H_2SO_4$ catalyzed pretreatment material, the $SO_2$-catalyzed pretreatment may provide a reasonable alternative to $H_2SO_4$ catalyzed pretreatment, even when the pretreated material is not washed and/or diluted before being fed to hydrolysis. Although the cost of $SO_2$ catalyzed pretreatment may be more than the cost of $H_2SO_4$ catalyzed pretreatment (e.g., due to the cost of $SO_2$ compared to $H_2SO_4$, and due to the required equipment, including $SO_2$ recovery) this cost may be offset by providing little to no washing and by the reduction in the amount of enzyme required. For example, preliminary experiments have indicated that $SO_2$ pretreatment may use less than 50% of the enzyme conventionally used for hydrolyzing $H_2SO_4$ catalyzed pretreated materials, while still providing a high glucose conversion.

In general, an efficient hydrolysis may exploit a relatively high glucose conversion, use less enzyme, and/or have shorter hydrolysis times. For example, referring again to FIG. 1, high efficiency hydrolysis of $SO_2$ catalyzed pretreated material is demonstrated by the high glucose conversion of the $SO_2$-washed sample, and/or by the fact that the $SO_2$ catalyzed washed sampled reached 0.8 glucose conversion in about 60 hours, while the $H_2SO_4$ catalyzed washed sample took 160 hours to reach 0.8 glucose conversion.

Figure 2:
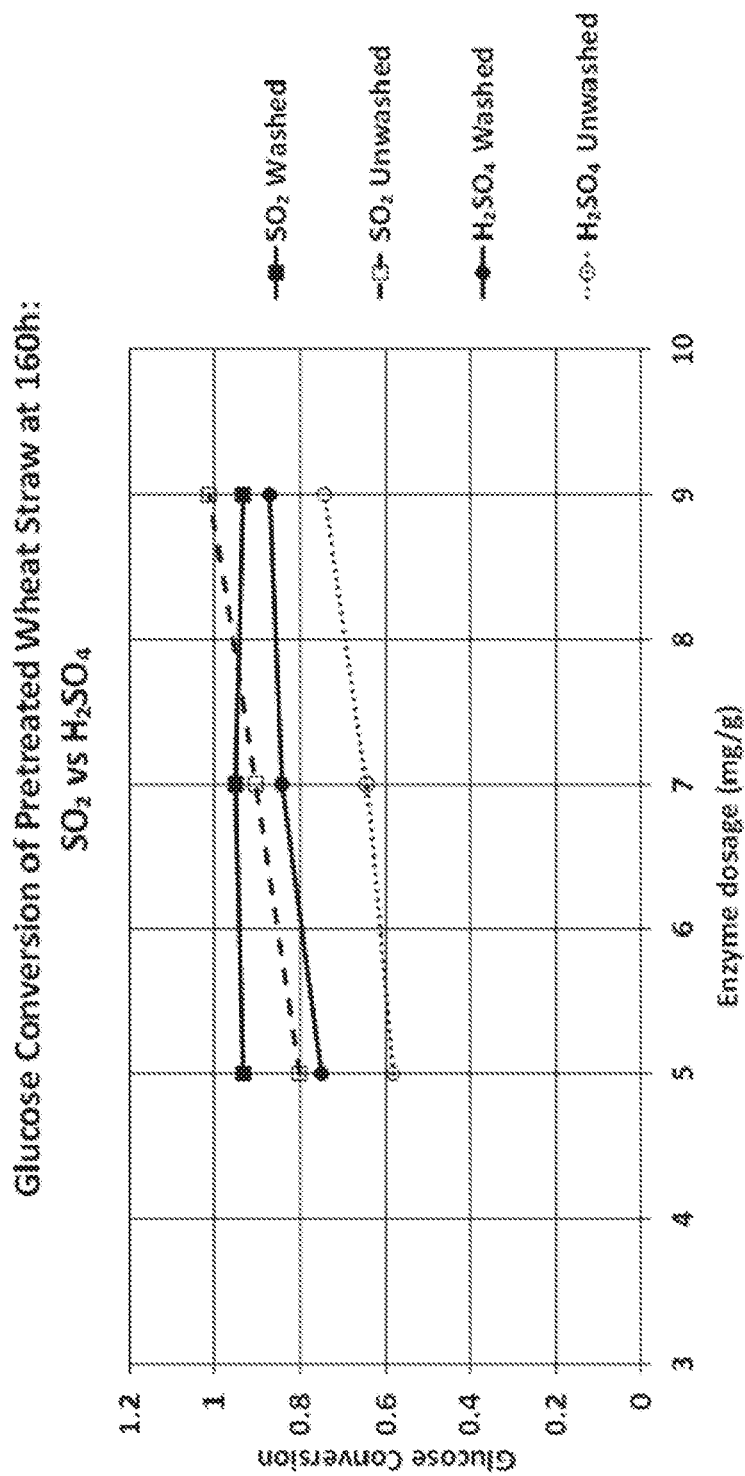
FIG. 2 is a dose-response curve of HPLC-measured glucose conversion.

Referring to FIG. 2, there is shown a plot of glucose conversion as a function of enzyme dosage (e.g., 5 mg/g, 7 mg/g, and 9 mg/g) measured from aliquots removed at time equal to 160 hours of hydrolysis, for both the washed and unwashed samples. Referring to the $H_2SO_4$ catalyzed pretreated washed and unwashed samples, a glucose conversion of about 0.75 requires almost twice the amount of enzyme for the unwashed sample (e.g., about 9 mg/g) as for the washed sample (e.g., about 5 mg/g). In contrast, referring to the $SO_2$ catalyzed pretreated washed and unwashed samples, a glucose conversion of at least 0.9 may be achieved using similar enzyme dosages for both the unwashed sample (e.g., about 8 mg/g) and the washed sample (e.g., about 8 mg/g). In this case, high efficiency of the hydrolysis is demonstrated by the fact that the enzymatic hydrolysis of the unwashed $SO_2$ catalyzed pretreated material with cellulase enzymes, performs almost as well as a hydrolysis conducted on the washed pretreated feedstock composition produced by the same pretreatment. In addition, high efficiency is demonstrated by the fact that a glucose conversion greater than about 0.9 may be obtained for the unwashed $SO_2$ catalyzed sample at an enzyme dosage of only 7 mg/g at 160 hours. In contrast, a similar glucose conversion level with the washed $H_2SO_4$ catalyzed sample requires a larger enzyme dosage (e.g., greater than 9 mg/g). Accordingly, a process that includes no or little washing/dilution of the pretreated material, and that requires less enzyme (e.g., relative to a conventional $H_2SO_4$ catalyzed pretreatment) may be provided.

As discussed above, conventional pretreatment of lignocellulosic feedstock with sulfuric acid produces a substrate that requires a relatively high dosage of cellulase enzyme to convert the cellulose to glucose, whereas $SO_2$ catalyzed pretreatment may produce a substrate that requires a relatively low dosage of cellulase enzyme (e.g., under 10 mg/g, under 7 mg/g, and in particular about 5 mg/g). However, it has also been found that the lignocellulosic feedstock may be pretreated in the presence of a mixture of sulfuric acid and sulfurous acid, and thus provide a substrate that requires a reduced amount of cellulase.

Example 10

$SO_2/H_2SO_4$ Catalyzed Pretreatment of Lignocellulosic Material

An $SO_2/H_2SO_4$ catalyzed batch pretreatment of wheat straw was conducted in 25 mL, stainless steel, laboratory tubular reactors (i.e., about 5 inches in length). The wheat straw was hammer-milled to 20 mesh and had a cellulose/glucan content of 34.61%, a lignin content of 20.49%, and a total solids (TS) content of 93.61%, w/w on a dry basis.

Each tubular reactor was charged with approximately 1.646 g of accurately weighed wheat straw, and various amounts of sulfurous acid ($\geq$6% $H_2SO_3$, from Sigma-Aldrich) and sulfuric acid (72% $H_2SO_4$), to provide a total contents weight of 13.4 g (i.e., a total slurry weight of 15 g at 10% solids consistency). The varying amounts of sulfuric acid and sulfurous acid were chosen so as to achieve a constant initial pH of about 2.00 (see Table 1). As sulfuric acid is a stronger acid than sulfurous acid, the maximum sulfuric acid usage was only 30% that of sulfurous acid by weight (e.g., (0.24/0.8)*100%).

Each tubular reactor was sealed, repeatedly shaken/inverted, and allowed rest for about 10 minutes before opening the reactor to measure the pH. The pretreatment reactor was then sealed and submerged in an oil bath preheated to 180° C. The tubular reactor remained immersed in the oil bath for 15 minutes (e.g., about 7 minutes included the temperature ramp up time, such that contents of the reactor were at 180° C. for about 8 minutes). At the end of the 15 minutes, the tubular reactor was removed from the oil bath and placed in an ice bath for 5 minutes. The contents of the tubular reactors (e.g., pretreated material) were removed, and filtered using a Buchner funnel and G6-grade glass microfiber filter paper.

The concentration of insoluble lignin was measured by measuring the lignin remaining after dissolution of the carbohydrates, using a carbohydrate assay based on Determination of Structural Carbohydrates and Lignin in Biomass-LAP (Technical Report NREL/TP-510-42618). The concentration of water-soluble lignin was determined by subtracting the insoluble lignin from the initial lignin concentration. The results are shown in Table 1.

TABLE 1

Pretreatment with mixtures of sulfuric acid and sulfurous acid

| Experiment | Sulfuric/sulfurous acid | Sulfuric acid (wt % of slurry) | Sulfurous acid (wt % of slurry) | pH after 10 minute soak | Soluble lignin (g/L) | Soluble lignin (% of initial lignin) |
|---|---|---|---|---|---|---|
| 1 | 100/0 | 0.24 | 0 | 1.98 | 4.29 | 19.56 |
| 2 | 75/25 | 0.18 | 0.20 | 1.98 | 5.69 | 26.07 |

TABLE 1-continued

Pretreatment with mixtures of sulfuric acid and sulfurous acid

| Experiment | Sulfuric/sulfurous acid | Sulfuric acid (wt % of slurry) | Sulfurous acid (wt % of slurry) | pH after 10 minute soak | Soluble lignin (g/L) | Soluble lignin (% of initial lignin) |
|---|---|---|---|---|---|---|
| 3 | 50/50 | 0.12 | 0.40 | 1.98 | 6.47 | 29.74 |
| 4 | 25/75 | 0.06 | 0.60 | 1.98 | 6.59 | 30.30 |
| 5 | 0/100 | 0 | 0.80 | 1.98 | 8.91 | 41.04 |

Referring to Table 1, the higher the concentration of sulfurous acid, the greater the degree of lignin dissolution. All of the pretreatment with sulfurous acid present achieved a higher level of lignin dissolution than experiment 1, which used only sulfuric acid. As a higher lignin dissolution may provide a better enzymatic hydrolysis of the cellulose, mixtures of sulfuric acid and sulfurous acid may perform better than sulfuric acid alone. Moreover, since the cost of sulfuric acid is lower than the cost of sulfur dioxide, a relatively good hydrolysis may be achieved at reduced cost.

Moreover, the benefits of using a combination of sulfuric acid and sulfurous acid/sulfur dioxide may be realized even without the soaking and/or dewatering steps. Without being bound by theory, the sulfuric acid may neutralize the alkalinity of the feedstock, while the sulfurous acid catalyzes the pretreatment reactions. For example, in one embodiment, sulfuric acid is sprayed onto the lignocellulosic feedstock, or is used to soak the lignocellulosic feedstock, prior to contact with $SO_2$/sulfurous acid. In any case, the combination of sulfuric acid and sulfurous acid/sulfur dioxide may provide improved efficiency in hydrolysis. Advantageously, this improved efficiency in hydrolysis may be exploited by using a reduced enzyme loading, having a reduced hydrolysis time, providing an increased cellulose conversion, or any combination thereof. In each case, the relatively high cost of sulfurous acid may be offset by the improved efficiency of the hydrolysis. For example, using a reduced enzyme loading reduces the cost of enzymes, which have been stated to be a significant contributor to the total cost of pretreatment.

Example 11

Determining the Glucan, Xylan, and Lignin Content

As described above, the cellulose/glucan content, xylan content, and/or lignin content discussed in Examples, 1, 2, and 10, was determined by a carbohydrate assay based on Determination_ of Structural Carbohydrate and Lignin in Biomass-LAP (Technical Report NREL/TP-510-42618). In particular, the carbohydrate assay was modified specifically for wheat straw and/or pretreated wheat straw. For example, the wheat straw sample was treated with 69 wt % sulfuric acid, wherein 1.5 mL of sulfuric acid is provided per 0.15 g of sample. The sample was incubated in a water bath at 50° C. for 30 minutes. An additional 43.5 mL water was added to bring the acid concentration up to 3.6 wt % $H_2SO_4$. The sample was then set in an autoclave set at 116° C. for 50 minutes. Once the sample was cooled, the determination of carbohydrate content, and in particular the sugar monomers, was determined using high performance liquid chromatograph (HPLC). A sugar recovery standard (SRS) containing known concentrations of arabinose, galactose, glucose, xylose, and 3.6% $H_2SO_4$ was taken also placed in an autoclave set 116° C. for 50 minutes, in order to account for losses due to decomposition of the sugars in the calculations. The corrected xylan and/or glucan content was determined using the following equation:

In particular, the xylan and glucan content was determined using the following equation:

$$\frac{Carbohydrate_{corrected}(\text{mg})}{\text{fiber g}} = \frac{\frac{\text{monomeric } sugar_{HPLC} \text{ (g/L)}}{\% \ R_{srs}/100} \times \text{Volume Diluted (mL)} \times \text{MW ratio}}{\text{Wt of sample (g)} \times \% \text{ total solids content}} \times 100$$

where $$\% \ R_{SRS} = \frac{(C_{sugar \ HPLC} \text{ (g/L) in } SRS)_{autoclaved}}{(C_{sugar \ HPLC} \text{ (g/L) in } SRS)_{nonautoclaved}} \times 100$$

$\% \ R_{SRS}$ = Percent recovery for individual sugar in sugar recovery standard $C_{sugar}$ = Concentration of individual sugar, and MW ratio = molecular weight ratio of polymeric sugar ($C_5$ or $C_6$) to monomeric sugar ($C_5$ or $C_6$)

For calculating xylan content, $$\text{MW ratio} = \frac{\text{MW repeating unit}}{2 \times \text{MW C5}} = \frac{\text{MW } C_{10}H_{16}O_8}{2 \times \text{MW } C_5H_{10}O_5} = \frac{264.23}{2 \times 150.13} = 0.88$$

For calculating glucan content, $$\text{MW ratio} = \frac{\text{MW repeating unit}}{2 \times \text{MW C6}} = \frac{\text{MW } C_{12}H_{20}O_{10}}{2 \times \text{MW } C_6H_{12}O_6} = \frac{324.28}{2 \times 180.15} = 0.90$$

The calculated lignin content corresponds to the acid-insoluble lignin.

Example 12

Measurement of Dissolved Solids in a Pretreated Feedstock Composition Compared to Dissolved Solids Fed to Hydrolysis The concentration of dissolved solids (weight of dissolved solids:weight liquid (w/w)) in the pretreated feedstock composition produced by pretreatment and in the pretreated feedstock composition fed to enzymatic hydrolysis are determined according to Example 5, for the $SO_2$ unwashed sample.

A percentage is then calculated from the two values to arrive at a value representing the percent of the concentration of dissolved solids in the pretreated feedstock composition fed to enzymatic hydrolysis relative to the concentration of dissolved solids in the pretreated feedstock composition after pretreatment.

Alternatively, the amount of dissolved solids in grams in the pretreated feedstock composition fed to enzymatic hydrolysis and that of the pretreated feedstock composition produced by pretreatment are determined. A percentage is then calculated from the two values to arrive at a value representing the percent of the dissolved solids in the pretreated feedstock composition resulting from pretreated that is fed to the subsequent step of enzymatic hydrolysis.

The percentage of dissolved solids in a pretreated feedstock composition fed to the enzymatic hydrolysis relative to the dissolved solids of the pretreated feedstock produced by the pretreatment may indicate the extent that the pretreated material is washed and/or diluted before being fed to hydrolysis.

For example, the pretreated material prepared according to Example 1, and analyzed according to methods in Examples 3, 4, and 5, was found to have a TS=33.67%, a UDS=19.76%, and a DS=13.91%.

Assuming full transfer of the dissolved solids when preparing the unwashed sample for hydrolysis according to Example 8, the percentage is calculated as follows. Using the method described in Example 5, the DS of the pretreated material was determined to be 13.91%. Accounting for the water added during lime addition, the DS becomes 13.32%. Taking into account dilution from the addition of buffer, make-up water, and enzyme solution, the DS introduced into hydrolysis was found to be 7.56%.

Accordingly, the dissolved solids concentration of the pretreated feedstock fed to hydrolysis (7.56%) was approximately 54.4% of the concentration of dissolved solids in the pretreated feedstock composition (i.e., 7.56%/13.91%).

Advantageously, providing a concentration of dissolved solids in a pretreated feedstock composition fed to the enzymatic hydrolysis that is at least 50% of the concentration of dissolved solids in the pretreated feedstock composition produced by $SO_2$ pretreatment may be consistent with providing little or no washing and/or dilution. However, the benefits of processes described herein may also be achieved when the pretreated feedstock composition fed to the enzymatic hydrolysis has a concentration that is at least about 35%, about 40%, or about 45% of the concentration of dissolved solids in the pretreated feedstock composition produced by $SO_2$ pretreatment. In one embodiment the pretreated feedstock composition fed to the enzymatic hydrolysis has a concentration that is at least about 55% of the concentration of dissolved solids in the pretreated feedstock composition produced by $SO_2$ pretreatment.

The present invention has been described with regard to one or more embodiments. However, it will be apparent to persons skilled in the art that a number of variations and modifications can be made without departing from the scope of the invention as defined in the claims.

The invention claimed is:

1. A process for producing a fermentation product from a lignocellulosic feedstock comprising:
  (i) soaking the lignocellulosic feedstock in a liquid comprising water to produce a soaked feedstock;
  (ii) at least partially dewatering the soaked feedstock to produce an at least partially dewatered feedstock;
  (iii) feeding the at least partially dewatered feedstock to a heating device;
  (iv) adding steam and acid to the heating device, said steam heating the at least partially dewatered feedstock to a first temperature to provide a heated feedstock, said acid comprising at least one of sulfur dioxide and sulfurous acid;
  (v) pretreating the heated feedstock in the presence of the acid in a pretreatment reactor to produce a pretreated feedstock, said pretreatment reactor disposed downstream of said heating device;
  (vi) hydrolyzing cellulose in the pretreated feedstock with cellulase enzymes to produce glucose, wherein the concentration of dissolved solids in the pretreated feedstock fed to the hydrolysis is at least about 50% of the concentration of dissolved solids in the pretreated feedstock produced in step (v); and
  (vii) fermenting the glucose to produce the fermentation product.

2. The process of claim 1, wherein the liquid comprises at least one of sulfur dioxide and sulfurous acid.

3. The process of claim 1, wherein the fermentation product is ethanol.

4. The process of claim 1, wherein the step of at least partially dewatering is conducted with a screw press.

5. The process of claim 1, comprising adding an inorganic alkali to the lignocellulosic feedstock subsequent to the pretreating and prior to the hydrolyzing to increase the pH of the pretreated feedstock, wherein the inorganic alkali comprises at least one of calcium hydroxide, ammonia, calcium carbonate, or potassium carbonate.

6. The process of claim 1, wherein the lignocellulosic feedstock comprises at least one of an agricultural residue, a biomass or energy crop, bagasse, sugar cane tops, or sugar cane leaves.

7. The process of claim 1, wherein the first temperature is between 170° C. and 230° C., and wherein the pretreating is conducted at about the first temperature.

8. The process of claim 1, wherein the pretreating is conducted at a pH less than 2.5.

9. The process of claim 1, wherein the pretreatment reactor has a residence time between 30 seconds and 30 minutes.

10. The process of claim 9, wherein the heating device has a residence time that is less than 1 minute.

11. The process of claim 1, wherein the heating device has a residence time that is about a time required to heat the at least partially dewatered feedstock in the heating device to a temperature that the pretreating is conducted at.

12. The process of claim 1, wherein the heating device has a residence time selected to minimize hydrolysis of hemicellulose in the at least partially dewatered feedstock within the heating device.

13. The process of claim 1, wherein the concentration of dissolved solids in the pretreated feedstock (w/w) fed to enzymatic hydrolysis is at least 55% of the concentration of dissolved solids (w/w) in the pretreated feedstock produced in step (vi).

14. The process of claim 1, wherein between the steps of soaking and hydrolyzing, the undissolved solids content of the lignocellulosic feedstock is between 15 wt % and 40 wt %.

15. The process of claim 1, wherein there is no solids-liquid separation between the steps of pretreating and hydrolyzing.

16. The process of claim 1, wherein the cellulose in the pretreated feedstock is substantially unwashed.

17. The process of claim 1, wherein the cellulose in the pretreated feedstock is substantially undiluted prior to hydrolyzing.

18. The process of claim 1, wherein the sulfur dioxide, sulfurous acid, or a combination thereof, are added to the lignocellulosic feedstock to provide an equivalent sulfur dioxide loading greater than about 10 wt %.

19. A process for producing a fermentation product from a lignocellulosic feedstock comprising:
  (i) feeding the lignocellulosic feedstock to at least one soaking tank, wherein the lignocellulosic feedstock is soaked in a liquid comprising water to produce a soaked feedstock;
  (ii) feeding the soaked feedstock to a dewatering device, wherein the soaked feedstock is at least partially dewatered to produce an at least partially dewatered feedstock having a consistency between 15 wt % and 40 wt %;
  (iii) feeding the at least partially dewatered feedstock to a heating device, wherein the at least partially dewatered feedstock is fluffed-up as it is conveyed therethrough, and wherein steam and acid are added to the at least partially dewatered feedstock to produce an acidified feedstock having a pH between 0.5 and 2.5, said acid comprising at least one of sulfur dioxide and sulfurous acid, a residence time of the heating device less than 1 minute;
  (iv) feeding the acidified feedstock to at least one pretreatment reactor disposed downstream of the heating device, wherein the acidified feedstock resides for a time between 30 seconds and 30 minutes at a temperature between 170° C. and 230° C. to produce a pretreated feedstock;
  (v) feeding the pretreated feedstock to at least one hydrolysis tank, wherein cellulose in the pretreated feedstock is hydrolyzed with cellulase to produce glucose, a concentration of dissolved solids in the pretreated feedstock fed to the hydrolysis at least about 50% of a concentration of dissolved solids in the pretreated feedstock produced in step (iv); and
  (vi) feeding a stream comprising the glucose to at least one fermentation tank, wherein the glucose is fermented to produce the fermentation product.

20. A system for producing a fermentation product from a lignocellulosic feedstock comprising:
  at least one tank for soaking the lignocellulosic feedstock in at least one of water and an aqueous solution;
  a dewatering device disposed downstream of the at least one tank for at least partially dewatering the soaked feedstock to produce an at least partially dewatered feedstock;
  a heating device disposed downstream of the dewatering device for fluffing up the at least partially dewatered feedstock, said heating device having at least one inlet for introducing steam and an acid to the at least partially dewatered feedstock, said acid comprising at least one of sulfur dioxide and sulfurous acid;
  at least one pretreatment reactor disposed downstream of the heating device, said at least one pretreatment reactor including at least one outlet for discharging a pretreated feedstock;
  at least one hydrolysis tank disposed downstream of said at least one outlet for hydrolyzing cellulose in the pretreated feedstock with cellulase enzymes to produce glucose;
  at least one system disposed between the at least one outlet and the at least one hydrolysis tank, said at least one system including at least one of a cooling system, a pH adjustment system, a solid liquid separator, a washing system, and a dilution system, said at least one system feeding the pretreated feedstock to the at least one hydrolysis tank such that a concentration of dissolved solids in the pretreated feedstock fed to the hydrolysis is at least about 50% of the concentration of dissolved solids in the pretreated feedstock produced by the at least one pretreatment reactor; and
  at least one fermentation tank disposed downstream of the at least one pretreatment reactor for fermenting the glucose to produce the fermentation product.

* * * * *

UNITED STATES PATENT AND TRADEMARK OFFICE
CERTIFICATE OF CORRECTION

PATENT NO. : 9,574,212 B2
APPLICATION NO. : 15/199638
DATED : February 21, 2017
INVENTOR(S) : Brian Foody et al.

It is certified that error appears in the above-identified patent and that said Letters Patent is hereby corrected as shown below:

On the Title Page

In Column 1 (page 2, item (56)) at Line 59, Under Other Publications, change "Saccharomuces" to --Saccharomyces--.

In Column 1 (page 3, item (56)) at Line 9, Under Other Publications, change "Techonologoy," to --Technology,--.

In Column 1 (page 3, item (56)) at Line 12, Under Other Publications, change "Biogengineering," to --Bioengineering,--.

In Column 1 (page 3, item (56)) at Line 14, Under Other Publications, change "Hydrolosis,"" to --Hydrolysis,"--.

In Column 1 (page 3, item (56)) at Line 20, Under Other Publications, change "Hydolysis" to --Hydrolysis--.

In Column 1 (page 3, item (56)) at Line 27, Under Other Publications, change "54-71," to --64-71,--.

In Column 1 (page 3, item (56)) at Line 38, Under Other Publications, change "Celllulose" to --Cellulose--.

In Column 1 (page 3, item (56)) at Line 40, Under Other Publications, change "386-991," to --986-991,--.

In Column 1 (page 3, item (56)) at Line 46, Under Other Publications, change "Charactisation,"" to --Characterization,"--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,574,212 B2

In Column 1 (page 3, item (56)) at Line 58, Under Other Publications, change "Autohydrolosys" to --Autohydrolysis--.

In Column 2 (page 3, item (56)) at Line 38, Under Other Publications, change "preteatment" to --pretreatment--.

In Column 2 (page 3, item (56)) at Line 39, Under Other Publications, change "fermnation" to --fermentation--.

In Column 2 (page 3, item (56)) at Line 63, Under Other Publications, change "Fermentaion,"" to --Fermentation,"--.

In Column 2 (page 3, item (56)) at Line 65, Under Other Publications, change "Hydrolosis" to --Hydrolysis--.

In the Specification

In Column 2 at Line 52, Change "cellulose" to --cellulase--.

In Column 8 at Line 4, After "dioxide" insert --and/or--.

In Column 8 at Line 54, Change "die" to --the--.

In Column 8 at Line 62, Change "my" to --may--.

In Column 11 at Line 28, Change "no" to --so--.

In Column 12 at Line 56, Change "(wlv)," to --(w/w),--.

In Column 19 at Line 63, After "mm)" insert --.--.

In Column 21 at Line 21, After "unwashed" insert --$SO_2$--.

In Column 22 at Line 39 (approx.), Change "gL)," to --g/L),--.

In Column 25 at Line 52, Change "Determination_" to --Determination--.